United States Patent
Wasicek et al.

(10) Patent No.: US 10,179,002 B2
(45) Date of Patent: Jan. 15, 2019

(54) APPARATUS AND METHOD FOR TREATING DISORDERS OF THE EAR, NOSE AND THROAT

(71) Applicant: Acclarent, Inc., Menlo Park, CA (US)

(72) Inventors: Lawrence D. Wasicek, San Jose, CA (US); Mathew D. Clopp, Santa Clara, CA (US); Ketan P. Muni, San Jose, CA (US); Howard L. Levine, Longboat Key, FL (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 14/699,148

(22) Filed: Apr. 29, 2015

(65) Prior Publication Data

US 2015/0327880 A1 Nov. 19, 2015

Related U.S. Application Data

(60) Provisional application No. 61/992,596, filed on May 13, 2014, provisional application No. 62/082,361, filed on Nov. 20, 2014.

(51) Int. Cl.
| | |
|---|---|
| *A61B 17/24* | (2006.01) |
| *A61B 17/26* | (2006.01) |
| *A61B 17/32* | (2006.01) |
| *A61B 17/22* | (2006.01) |
| *A61B 17/3205* | (2006.01) |
| *A61B 18/14* | (2006.01) |
| *A61B 18/12* | (2006.01) |

(Continued)

(52) U.S. Cl.
CPC ........ *A61B 17/32002* (2013.01); *A61B 17/22* (2013.01); *A61B 17/3205* (2013.01); *A61B 17/320783* (2013.01); *A61B 18/1206* (2013.01); *A61B 18/1485* (2013.01); *A61B 2017/00017* (2013.01); *A61B 2017/22079* (2013.01); *A61B 2017/320064* (2013.01); *A61B 2018/00077* (2013.01); *A61B 2018/00172* (2013.01); *A61B 2018/00327* (2013.01)

(58) Field of Classification Search
CPC ........ A61B 17/32002; A61B 2217/005; A61B 17/32; A61B 17/3205; A61B 17/320783; A61B 17/320758; A61B 2017/320064; A61B 2017/320032; A61B 17/320016; A61B 2018/00327
USPC ................ 606/110, 115, 159, 167, 170, 180
See application file for complete search history.

(56) References Cited

U.S. PATENT DOCUMENTS

| | | | | |
|---|---|---|---|---|
| 5,269,785 | A | * | 12/1993 | Bonutti ................ A61B 10/025 606/167 |
| 5,364,395 | A | | 11/1994 | West, Jr. |

(Continued)

FOREIGN PATENT DOCUMENTS

WO     WO 96/29942 A1     10/1996

OTHER PUBLICATIONS

Written Opinion of the International Searching Authority, International Application No. PCT/US2015/027049, dated Nov. 2015.

(Continued)

*Primary Examiner* — Katherine M Shi

(57) ABSTRACT

Apparatus for use in surgeries to treat disorders of the ear, nose, and throat including a hand-held device and rotating blade assembly. The apparatus may be connected to a vacuum source. A method of use is also disclosed.

29 Claims, 16 Drawing Sheets

(51) Int. Cl.
*A61B 17/3207* (2006.01)
*A61B 17/00* (2006.01)
*A61B 18/00* (2006.01)

(56) References Cited

U.S. PATENT DOCUMENTS

| | | | |
|---|---|---|---|
| 5,624,457 A | 4/1997 | Farley et al. | |
| 5,632,755 A | 5/1997 | Nordgren et al. | |
| 5,916,231 A * | 6/1999 | Bays | A61B 17/32002 604/22 |
| 6,251,120 B1 * | 6/2001 | Dorn | A61B 17/32002 606/170 |
| 6,530,926 B1 | 3/2003 | Davison | |
| 6,533,749 B1 * | 3/2003 | Mitusina | A61B 17/32002 604/22 |
| 2004/0059363 A1 * | 3/2004 | Alvarez | A61B 17/32002 606/170 |
| 2005/0065538 A1 * | 3/2005 | Van Wyk | A61B 17/32002 606/159 |
| 2005/0096649 A1 | 5/2005 | Adams | |
| 2006/0200123 A1 * | 9/2006 | Ryan | A61B 18/148 606/48 |
| 2008/0200941 A1 * | 8/2008 | Mitusina | A61B 17/32002 606/171 |
| 2010/0030216 A1 * | 2/2010 | Arcenio | A61B 17/32002 606/79 |
| 2010/0298855 A1 * | 11/2010 | Dierck | A61B 17/32002 606/170 |
| 2012/0143175 A1 * | 6/2012 | Hermann | A61B 17/1631 606/1 |
| 2013/0103067 A1 * | 4/2013 | Fabro | A61B 17/3207 606/170 |
| 2013/0345704 A1 * | 12/2013 | Palmer | A61B 18/148 606/46 |
| 2014/0100567 A1 | 4/2014 | Edwards et al. | |
| 2014/0371718 A1 * | 12/2014 | Alvarez | A61M 25/0074 604/510 |

OTHER PUBLICATIONS

International Search Report dated Nov. 24, 2015, International Application No. PCT/US2015/027049.
International Preliminary Report on Patentability dated Nov. 15, 2016, International Application No. PCTUS2015/027049.
Written Opinion of the International Searching Authority, International Application No. PCT/US2015/027041, dated Nov. 2015.
International Search Report dated Aug. 7, 2015, International Application No. PCT/US2015/027041.
International Preliminary Report on Patentability dated Nov. 15, 2016, International Application No. PCTUS2015/027041.

* cited by examiner

APPARATUS AND METHOD FOR TREATING DISORDERS OF THE EAR, NOSE AND THROAT

TECHNICAL FIELD

The present disclosure relates generally to surgical instruments and methods and, more particularly, to surgical instruments for use in surgeries to treat disorders of the ear, nose, and throat.

BACKGROUND

Functional endoscopic sinus surgery (FESS) is a common type of surgery used to treat chronic sinusitis, as well as remove tumors, polyps and other aberrant growths from the nose. In a typical FESS procedure, an endoscope is inserted into the nostril along with one or more surgical instruments. The endoscope typically provides the surgeon with a direct line-of-sight view to permit the surgeon to visualize a number of relevant anatomical structures within the surgical field. Under visualization through the endoscope, the surgeon may remove diseased or hypertrophic tissue or bone and/or enlarge the ostia of the sinuses to restore normal drainage of the sinuses. A number of surgical instruments may be used to cut and remove tissue and/or bone, cauterize, suction, etc. during a FESS procedure.

Nasal polyp surgery is one type of FESS procedure that is typically performed in an operating room with the patient under general anesthesia. It typically involves a powered fixed piece of capital equipment that includes a console and a hand piece. This equipment usually requires electrical, vacuum, and saline hookups. This surgical method is highly invasive and requires substantial recovery time for the patient Nasal polyps can also be removed in the physician's office with simple tools such as forceps. The patient is typically awake during the procedure. The physician is limited by what he can comfortably reach and remove without creating too much discomfort to the patient. This procedure is relatively limited in the ability to remove substantial nasal polyps.

Another removal tool is a microdebrider, which is a rotary cutting tool that may be used to shave tissue and/or bone. Microdebriders may be connected to a vacuum source, which may be used to create suction that remove excess blood and tissue from the surgical field.

SUMMARY

According to one aspect of the disclosure, a surgical instrument and method for performing an ear, nose, and throat surgery is disclosed. The surgical instrument includes a hand piece and an outer shaft coupled to the hand piece that extends to a distal end. The outer shaft has a rounded, convex distal surface and a first plurality of cutting teeth defined at the distal end. The instrument also includes an inner shaft positioned in the outer shaft. The inner shaft has a passageway and a second plurality of cutting teeth. The surgical instrument includes a cutting slot that is partially defined by the first plurality of cutting teeth, and the inner shaft is configured to rotate relative to the outer shaft such that the first plurality of cutting teeth and the second plurality of cutting teeth cooperate to cut tissue advanced into the passageway through the cutting slot.

In some embodiments, the outer shaft may include a cylindrical outer surface that extends along a longitudinal axis of the outer shaft to the rounded, convex distal surface, and the cutting slot may be defined in the cylindrical outer surface. In some embodiments, the second plurality of cutting teeth may be axially aligned with the cutting slot.

Additionally, in some embodiments, the rounded, convex distal surface may extend from a distal apex to a proximal edge, and the proximal edge of the convex distal surface may define a distal end of the cutting slot. The proximal edge of the rounded, convex distal surface may be one of a chamfered edge and a rounded edge.

In some embodiments, the cutting slot may extend to a proximal end defined by a distal edge of an outer surface of the outer shaft, the proximal edge of the convex distal surface and the distal edge of the outer surface of the outer shaft may cooperate to define a curved imaginary plane, and the first plurality of cutting teeth may be recessed below the curved imaginary plane.

In some embodiments, the distal edge of the outer surface may be one of a chamfered edge and a rounded edge. In some embodiments, each cutting tooth of the first plurality of cutting teeth may include a planar outer surface.

Additionally, in some embodiments, the hand piece may include a connector configured to be coupled to a negative pressure source to fluidly connect the passageway of the inner shaft to the negative pressure source.

In some embodiments, the surgical instrument may also include a drive mechanism configured to rotate the inner shaft relative to the outer shaft. In some embodiments, the drive mechanism may include an electric motor positioned in the hand piece. In some embodiments, the drive mechanism may include a cable drive mechanism configured to be coupled to the hand piece.

In some embodiments, the outer shaft and the inner shaft may be removably coupled to the hand piece. Additionally, in some embodiments, the instrument may further include a hub coupled to the outer shaft. The hub may include a plurality of splines engaged with the hand piece to secure the outer shaft to the hand piece. In some embodiments, the instrument may include a second hub coupled to the inner shaft. The second hub may include a second plurality of splines engaged with the hand piece to pivotally couple the inner shaft to the hand piece.

According to another aspect, a surgical instrument includes a hand piece, a first shaft coupled to the hand piece, and a second shaft positioned in the first shaft. The first shaft includes a cylindrical outer surface extending along a longitudinal axis of the first shaft to an atraumatic tip, a closed distal end, and a cutting slot defined in the cylindrical outer surface adjacent to the closed distal end. The second shaft has a plurality of cutting teeth axially aligned with the cutting slot, and the second shaft is configured to rotate relative to the first shaft such that the plurality of teeth cut tissue in the cutting slot.

In some embodiments, the closed distal end of the first shaft may define a spherical tip. Additionally, in some embodiments, the second shaft may include a spherical distal tip.

In some embodiments, the first shaft may be formed from a first material and the second shaft is formed from a second material different from the first material. In some embodiments, a distal section of the first shaft may be malleable.

In some embodiments, the distal section of the first shaft may include a plurality of slots defined in the first shaft. In some embodiments, a proximal section of the first shaft may be substantially rigid.

In some embodiments, a distal section of the second shaft may be flexible. In some embodiments, a proximal section of the second shaft may be substantially rigid.

According to another aspect, a surgical cutting tool is disclosed. The surgical cutting tool comprises a first shaft including a cylindrical outer surface extending along a longitudinal axis of the first shaft, a first passageway extending along the longitudinal axis from an open proximal end to a closed distal end, and a cutting slot extending inward from the cylindrical outer surface to the first passageway. The cutting slot is positioned adjacent to the closed distal end. The surgical cutting tool also includes a second shaft positioned in the first passageway of the first shaft. The second shaft has a second passageway and a cutting edge that is axially aligned with the cutting slot. The second shaft is configured to rotate relative to the first shaft such that the cutting edge cuts tissue advanced into the second passageway through the cutting slot.

In some embodiments, the cutting slot may be partially defined by a plurality of cutting teeth, and the cutting edge and the plurality of cutting teeth may cooperate to cut tissue advanced into the second passageway through the cutting slot when the second shaft is rotated. In some embodiments, the plurality of cutting teeth may be a first plurality of cutting teeth, and the cutting edge includes a second plurality of cutting teeth.

Additionally, in some embodiments, the plurality of cutting teeth may be recessed from the cylindrical outer surface. In some embodiments, the first shaft may include a distal section that defines a first diameter and a proximal section that defines a second diameter greater than the first diameter.

BRIEF DESCRIPTION OF THE DRAWINGS

The detailed description particularly refers to the following figures, in which.

DETAILED DESCRIPTION OF THE DRAWINGS

Figure 1:
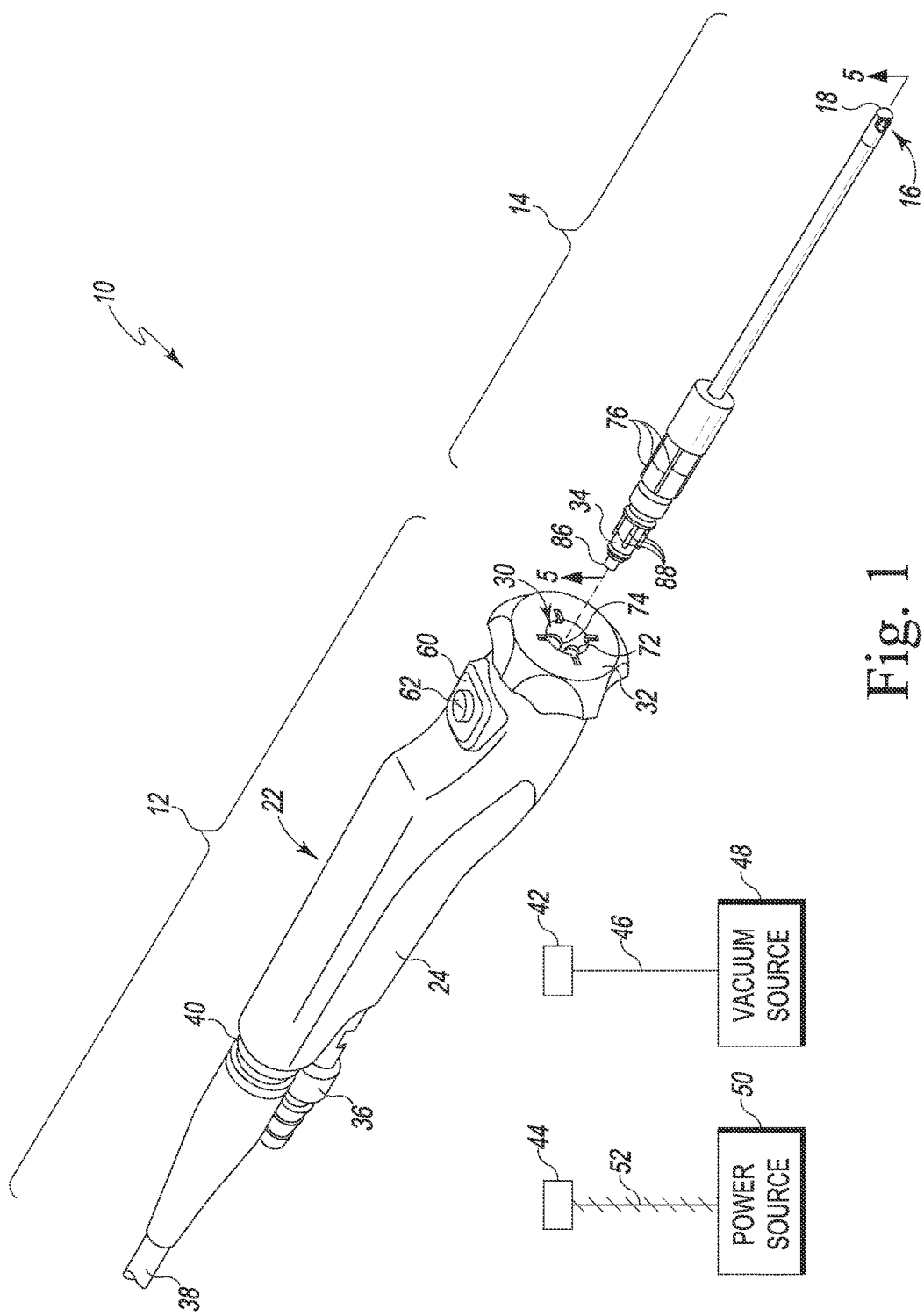
FIG. 1 is an exploded perspective view of one embodiment of a surgical instrument for use in surgeries to treat disorders of the ear, nose, and throat.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIG. 1, a surgical instrument 10 for use in surgeries to treat disorders of the ear, nose, and throat including, for example, nasal polyp surgery is shown. The instrument 10 includes a hand piece 12 and a blade assembly 14 configured to be coupled to the hand piece 12. The blade assembly 14 includes a cutting slot 16 that is positioned at its distal end 18.

When the instrument 10 is used to remove diseased or damaged tissue from a patient, the distal end 18 of the blade assembly 14 may be advanced into a nasal passage. The instrument 10 may be operated to position the target tissue within the cutting slot 16 and shave or cut the target tissue. Suction may then be used to remove the severed tissue, as described in greater detail below.

The hand piece 12 of the surgical instrument 10 includes an elongated body 22 and a grip 24 formed on the body 22. The grip 24 is configured to be grasped by a user during operation of the surgical instrument 10. In other embodiments, the hand piece may include a handle or may include one or more ergonomic features to facilitate use of the instrument 10. The elongated body 22 and the grip 24 may be formed from the same material such as, for example, a plastic, rigid polymer, or other rigid materials suitable for autoclaving. The grip 24 may also be formed from a soft or padded material such as neoprene. In some embodiments, the hand piece 12 may be wholly or partially covered by a disposable outer skin or wrap during surgery such that the hand piece 12 does require re-sterilization or autoclaving between surgeries. In other embodiments, the hand piece 12 may be configured to be disposable after a single-use.

The hand piece 12 includes an aperture 30 defined in a longitudinal end 32 of the elongated body 22. As shown in FIG. 1, the aperture 30 is sized to receive a proximal end 34 of the blade assembly 14. The hand piece 12 also includes a connector 36 and a connector cable 38 positioned at the opposite longitudinal end 40 of the body 22. The connector 36 and the cable 38 are configured to be coupled with corresponding connectors 42, 44 of a negative pressure source and an electrical cable 52, respectively.

The connector 42 extends from a hose 46 that is connected to a source of negative pressure such as, for example, vacuum pump 48. The connector 36 of the hand piece 12 is configured to engage the hose connector 42 such that the hand piece 12 (and hence the blade assembly 14) may be connected to the vacuum pump 48. It should be appreciated that in other embodiments the negative pressure source may take the form of an air compressor, or other suction device.

In the illustrative embodiment, the electrical cable 52 includes the connector 44, which is coupled to a power source 50 such as, for example, a standard domestic power outlet. The power source 50 is configured to supply electrical power to the hand piece 12. The cable 38 of the hand piece 12 includes a connector (not shown) that is configured to engage the connector 44. In that way, electrical power may be supplied from the source 50 to the electrically-operated components (see FIG. 2) of the hand piece 12.

As shown in FIG. 1, the hand piece 12 also includes a control panel 60 positioned on the elongated body 22. In the illustrative embodiment, the control panel 60 includes a single control button 62, which may be toggled to operate the surgical instrument 10. In other embodiments, the hand piece 12 may include additional controls such as toggles, levers, or other buttons to individually activate the electrically-operated components of the instrument 10 and/or the vacuum pump 48. It should also be appreciated that in other embodiments the control panel 60 may be omitted from the hand piece 12, and the instrument 10 and/or the vacuum pump 48 may be activated using a foot pedal or other control device.

In still other embodiments, the negative pressure source may be integrated into a portable console. Similarly, the power source may be included in a surgical console. The hand piece 12 may be configured to be plugged into a wall electrical socket via a plug or adaptor. The hand piece 12 may also be configured to be battery-powered.

Figure 2:
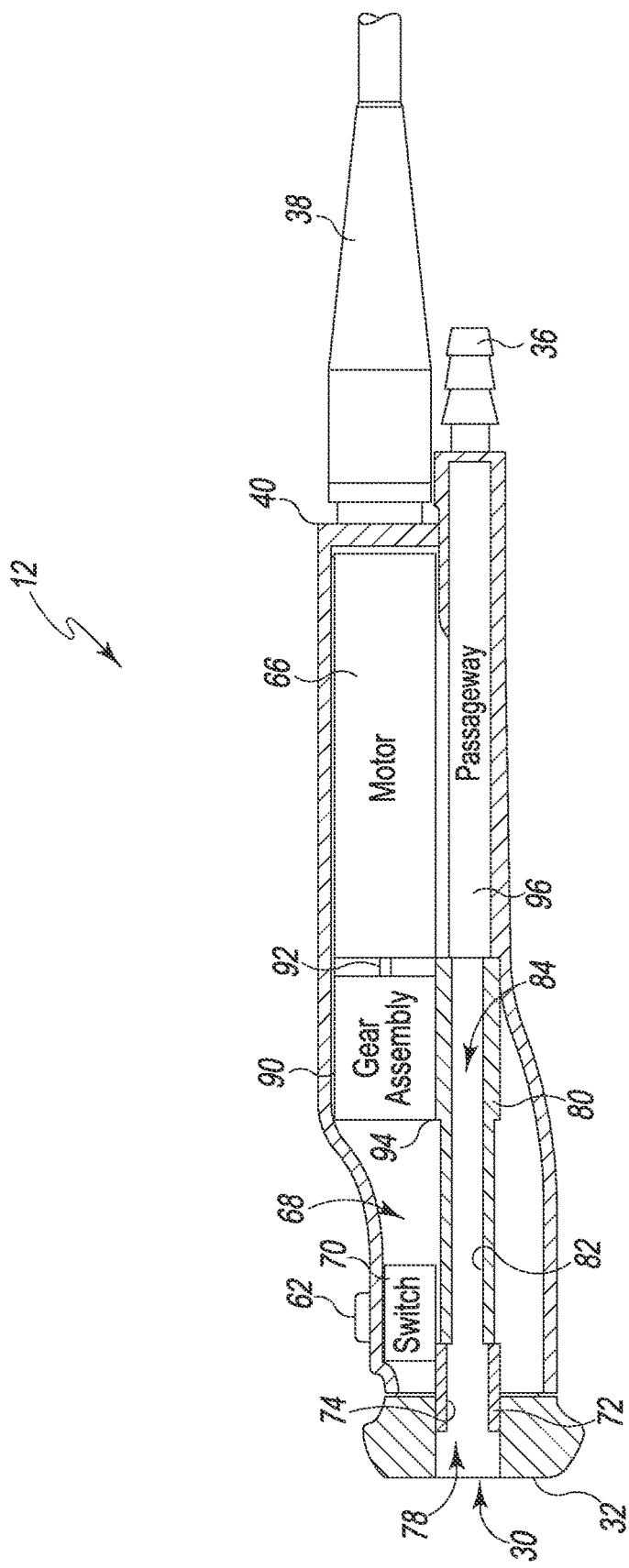
FIG. 2 is a cross-sectional elevation diagrammatic view of a hand-held device of the surgical instrument of FIG. 1.

Referring now to FIG. 2, the hand piece 12 includes an electric motor 66 that is positioned in an inner chamber 68 of the elongated body 22. In the illustrative embodiment, the motor 66 is an electric motor powered by direct current (DC). In other embodiments, the motor 66 may be powered by alternating current (AC). An electrical contact switch 70 is positioned in the chamber 68 below the button 62. When the button 62 is toggled or pressed by the user, the switch 70 is configured to generate an electrical output. The electrical output is relayed to the pump 48 and the power source 50 via the cable 52, thereby activating the pump 48 and energizing the motor 66.

As described above, the hand piece 12 is configured to receive the blade assembly 14. In the illustrative embodiment, the hand piece 12 of the surgical instrument 10 includes a mounting collar 72, which receives the proximal end 34 of the blade assembly 14. As shown in FIGS. 1-2, the mounting collar 72 is positioned in the aperture 30 of the hand piece 12. The mounting collar 72 illustratively includes a splined surface 74 that defines a passageway 78. When the proximal end 34 of the blade assembly 14 is seated in the aperture 30, the blade assembly 14 extends through the passageway 78 and a set of splines 76 defined on the blade assembly 14 engage the splined surface 74. In that way, the blade assembly 14 is secured to the hand piece 12. In other embodiments, the mounting collar 72 and the blade assembly 14 might include corresponding threads to secure the assembly 14 to the hand piece 12. In still other embodiments, a combination of pins, slots, or other fastening devices may be used to secure the assembly 14 to the hand piece 12. It should also be appreciated that in other embodiments part (or all) of the blade assembly may be permanently fixed to the hand piece.

While the mounting collar 72 is fixed in position relative to the elongated body 22, the hand piece 12 also includes an inner collar 80 that is pivotally coupled to the body 22. In the illustrative embodiment, the collar 80 is mounted within the chamber 68 of the body 22 on bearings (not shown), which permit the inner collar 80 to rotate within the body 22. The inner collar 80, like the collar 72, includes a splined surface 82 that defines a passageway 84. When the proximal end 34 of the blade assembly 14 is seated in the aperture 30, the proximal tip 86 of the blade assembly 14 is positioned in the passageway 84 and a set of splines 88 defined on the blade assembly 14 engage the splined surface 82 of the collar 80.

A gear assembly 90 is positioned between the motor 66 and the inner collar 80 to transmit the output of the motor 66 to the collar 80 (and hence the spline 88 of the blade assembly 14). In the illustrative embodiment, the gear assembly 90 is coupled to an output shaft 92 of the motor. The gear assembly 90 includes a plurality of teeth (not shown), which are configured to engage a corresponding set of teeth (not shown) defined on the outer surface 94 of the inner collar 80. The gear assembly 90 may include one or more gears such as, for example, helical, bevel, worm, or other devices configured to transmit the output of the motor to the collar 80.

When the motor 66 is energized, the motor 66 causes the output shaft 92 to rotate. The rotation of the shaft 92 is transmitted to the collar 80 via the gear assembly 90, thereby causing the inner collar 80 to rotate. As described in greater detail below, the rotation of the collar 80 causes an inner blade shaft 100 of the blade assembly 14 to rotate when the blade assembly 14 is secured to the hand piece 12.

The hand piece 12 also includes a passageway 96 that is positioned between the connector 36 and the inner collar 80. The passageway 96 fluidly couples the passageway 84 of the inner collar 80 to the connector 36. In that way, the passageway 84 may be exposed to negative pressure when the vacuum pump 48 is activated.

Figure 3:
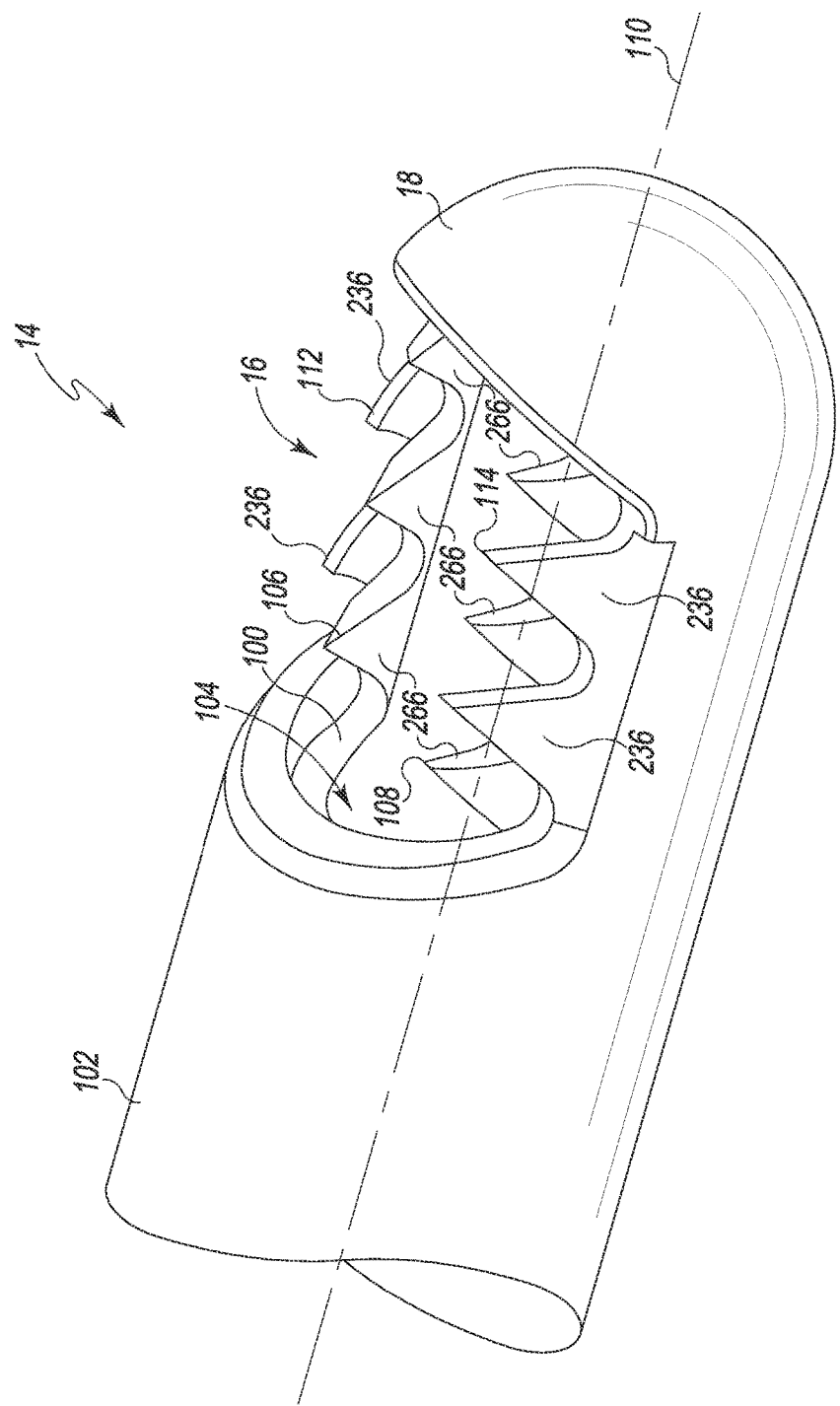
FIG. 3 is a perspective view of the distal end of a blade assembly of the surgical instrument of FIG. 1.
Figure 4:
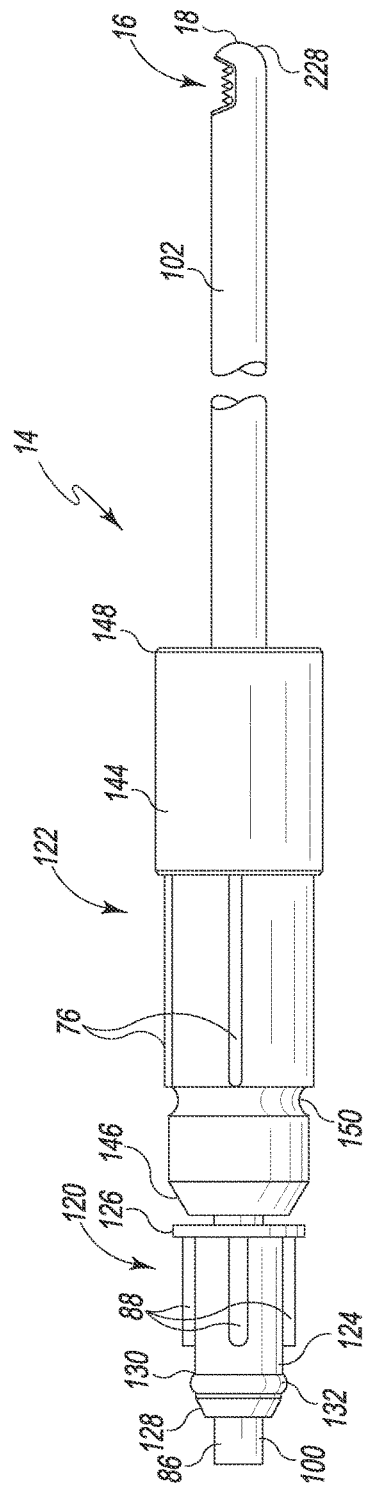
FIG. 4 is a side elevation view of the blade assembly of FIG. 3.
Figure 5:
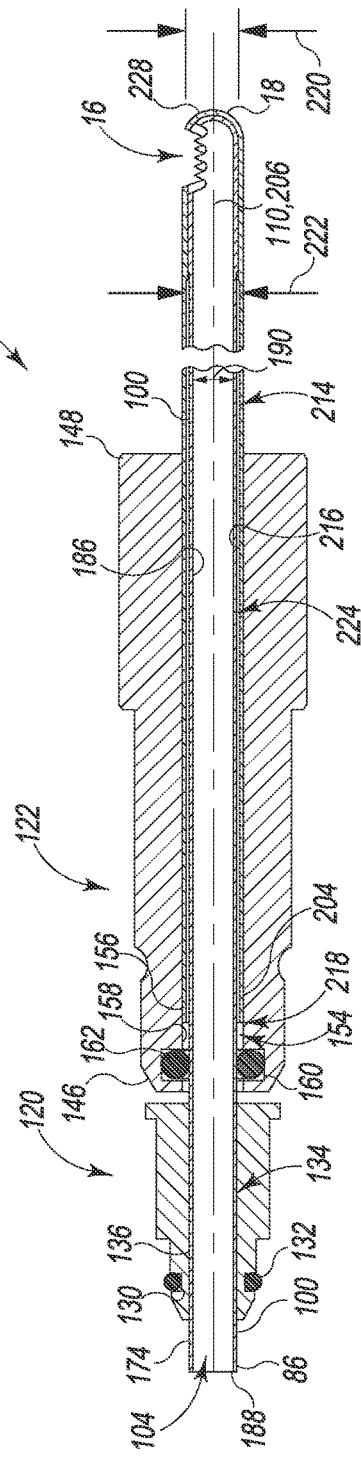
FIG. 5 is a cross-sectional side elevation view of the blade assembly taken along the line 5-5 in FIG. 1.

As described above, the surgical instrument 10 includes a blade assembly 14, which is the cutting tool of the surgical instrument 10. Referring now to FIGS. 3-5, the blade assembly 14 includes the inner blade shaft 100, which is positioned within an outer blade shaft 102. As described above, the blade assembly 14 includes a cutting slot 16 into which tissue may be placed to be shaved or cut. As shown in FIG. 3, the cutting slot 16 is defined in the outer blade shaft 102, and the inner blade shaft 100 includes a longitudinal passageway 104 that opens into the cutting slot 16.

The inner blade shaft 100 also includes cutting edges 106, 108 that are axially aligned with the cutting slot 16. The edges 106, 108 are configured to cut or shaft tissue placed in the cutting slot 16. As described in greater detail below, when the inner blade shaft 100 is rotated about its longitudinal axis 110, tissue advanced into the cutting slot 16 may be sliced by the cutting edge 106 or the cutting edge 108. In the illustrative embodiment, the outer blade shaft 102 also includes a pair of cutting edges 112, 114, which cooperate with the cutting edges 106, 108 of the inner blade shaft 100 to slice the tissue. The severed tissue may then be drawn into the longitudinal passageway 104 of the inner blade shaft 100 by suction.

As shown in FIG. 4, the blade shafts 100, 102 are attached to an inner hub 120 and an outer hub 122, respectively. In the illustrative embodiment, the hubs 120, 122 are each formed from rigid material such as, for example, a metallic material, plastic, or rigid polymer. The inner hub 120 is positioned at the proximal end 34 of the blade assembly 14 and includes a cylindrical outer surface 124 that extends from an end 126 positioned adjacent to the outer hub 122 to an end 128. The plurality of splines 88 are positioned at the end 126 and extend outwardly from the surface 124. As described above, the splines 88 are configured to engage the splined surface 82 of the inner collar 80 of the hand piece 12 when the blade assembly 14 is secured thereto. In that way, the inner hub 120 may be rotated with the collar 80 when the motor 66 is energized.

The inner hub 120 also has an annular groove 130 that is defined in the cylindrical outer surface 124 at the end 128. A seal such as, for example, an elastomeric o-ring 132 is positioned in the groove 130. When the blade assembly 14 is positioned in the aperture 30 of the hand piece 12, the o-ring 132 engages a portion of the surface 82 of the inner collar 80 to create an air-tight barrier. It should be appreciated that in other embodiments the seal may be omitted from the blade assembly 14, and the hand piece 12 may include an o-ring or other seal that engages the inner hub.

As shown in FIG. 5, a longitudinal bore 134 extends through the inner hub 120. The bore 134 is sized to receive a proximal section 136 of the inner blade shaft 100. In the illustrative embodiment, the inner blade shaft 100 is press-fit into the bore 134. In other embodiments, a combination of splines, slots, pins, welding, swaging, or other fasteners may be used to secure the hub 120 to the shaft 100. It should be appreciated that the hub 120 and/or the shaft 100 may configured for disassembly and reuse. In other embodiments, the hub 120 may be permanently fixed to the shaft 100. As shown in FIGS. 4-5, the inner blade shaft 100 extends outwardly from the inner hub 120 to define the proximal tip 86 of the blade assembly 14.

The outer hub 122 of the blade assembly 14 is positioned distal of the inner hub 120. As shown in FIG. 4, the hub 122 includes a cylindrical outer surface 144 that extends from an end 146 positioned adjacent to the inner hub 120 to an end 148. The plurality of splines 76 extend outwardly from the surface 144. As described above, the splines 76 are configured to engage the splined surface 74 of the mounting collar 72 of the hand piece 12 when the blade assembly 14 is secured thereto. In that way, the outer hub 122 is fixed relative to the hand piece 12 and hence does not rotate with the inner hub 120.

The outer hub 122 also has an annular groove 150 that is defined in the cylindrical outer surface 144 adjacent to the end 146. The groove 150 is configured to receive a seal such as, for example, an elastomeric o-ring. that is secured to the mounting collar 72. In the illustrative embodiment, the hand piece 12 includes an elastomeric o-ring (not shown), which is positioned in the groove 150 when the blade assembly 14 is positioned in the aperture 30 of the hand piece 12. It should be appreciated that in other embodiments the seal may be attached to the outer hub 122.

As shown in FIG. 5, a longitudinal bore 154 extends through the outer hub 122. The bore 154 is sized to receive a proximal section 156 of the outer blade shaft 102. In the illustrative embodiment, the outer blade shaft 102 is press-fit into the bore 154. In other embodiments, a combination of splines, slots, pins, welding, swaging, and other fasteners may be used to secure the hub 122 to the shaft 102. It should be appreciated that the hub 122 and/or the shaft 102 may configured for disassembly and reuse. In other embodiments, the hub 122 may be permanently fixed to the shaft 102.

The longitudinal bore 154 of the outer hub 122 is defined by a cylindrical inner surface 158. The outer hub 122 also has an annular groove 160 that is defined in the surface 158 at the end 148. A seal such as, for example, an elastomeric o-ring 162 is positioned in the groove 160. As shown in FIG. 5, the o-ring 162 engages the proximal section 136 of the inner blade shaft 100. In the illustrative embodiment, the seal 162 facilitates the positioning of the inner blade shaft 100 within the outer blade shaft 102. It should be appreciated that in other embodiments the seal may be omitted. In other embodiments, the blade assembly 14 may include a bearing or other device that aligns the inner blade shaft 100 with the outer blade shaft 102.

The blade assembly 14 has a length defined between the distal end 18 and the proximal tip 86. In the illustrative embodiment, the length of the blade assembly is between about 11 centimeters and about 12 centimeters. It should be appreciated the blade assembly 14 may be longer or shorter depending on the nature of the surgery and the anatomy of a particular patient.

Figure 6:
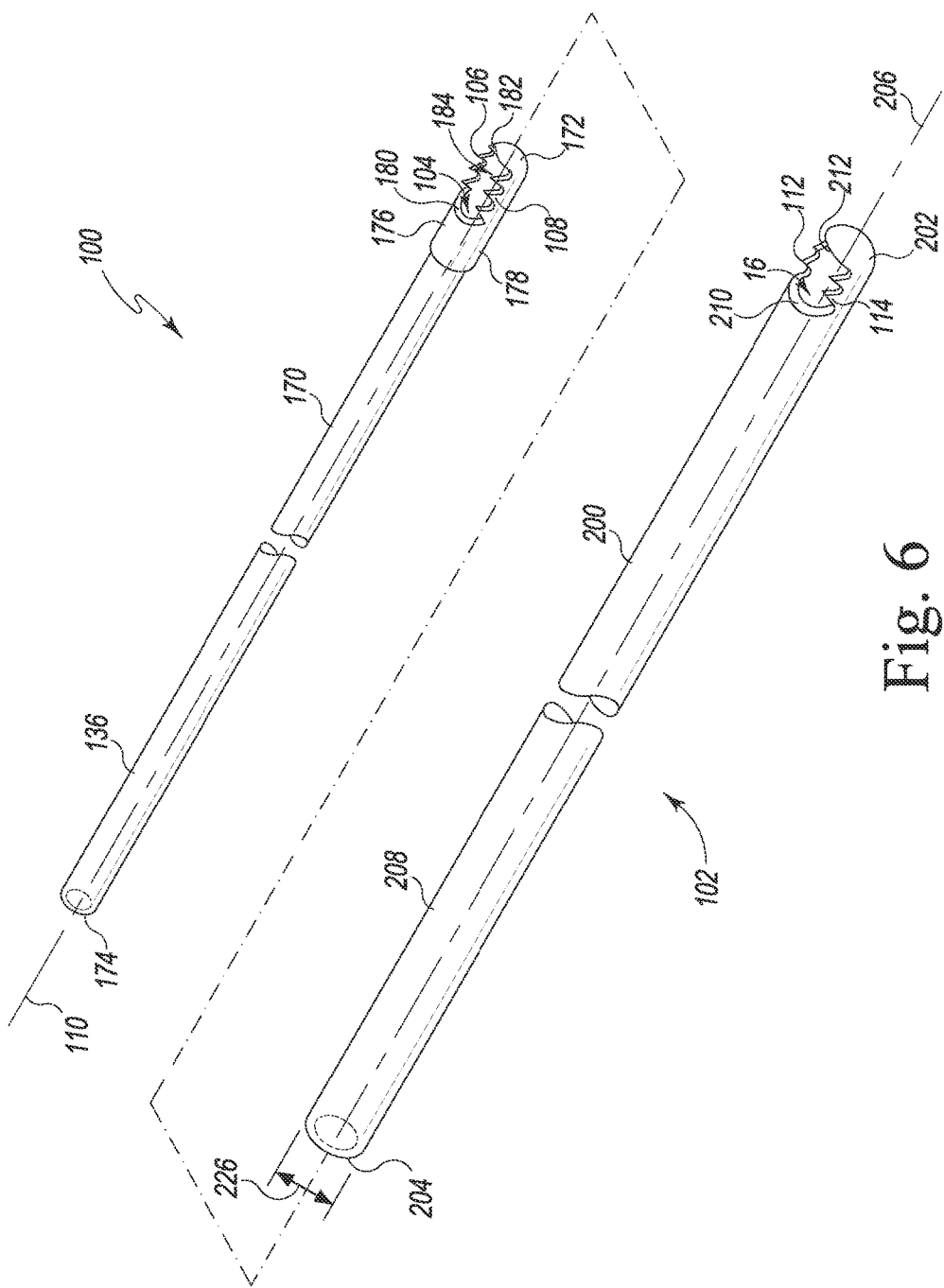
FIG. 6 is an exploded perspective view of the inner and outer blade shafts of the blade assembly of FIGS. 3-5.

Referring now to FIG. 6, the inner blade shaft 100 has an elongated tube 170 that extends from a distal end 172 to a proximal end 174. The tube 170 includes a cylindrical proximal section 136 and a distal section 176. The distal section 176 includes a cylindrical outer surface 178, which has an outer diameter that is larger than the outer diameter of the proximal section 136. In the illustrative embodiment, the distal section 176 is stepped relative to the proximal section 136. In other embodiments, the tube 170 may include multiple step sections or taper along its length. In still other embodiments, the outer diameter of the proximal section may be larger than the outer diameter of the distal section to, for example, facilitate suction and reduce the possibility of clogging in certain applications.

In the illustrative embodiment, the proximal section 136 of the elongated tube 170 is formed from a bio-compatible metallic material such as, for example, stainless steel, and the distal section 176 is formed from a bio-compatible surgical steel such as, for example a high carbon steel or nickel alloy that is welded, press fit, or swaged to the proximal section 136. In that way, the distal section 176 is formed as a hardened steel tip of the tube 170. In other embodiments, the tube 170 may be formed from a plastic or other rigid polymer.

Additionally, the sections 136, 138 of the shaft 100 may formed separately from the same metallic material and later assembled by welding, press fit, or swaging. In other embodiments, the sections 136, 138 may be formed as a single, monolithic component or the shaft 100 may be formed from additional pieces that are later assembled. Additionally, the sections 136, 138 may be formed from different materials. For example, the distal section 138 may be formed from a flexible or semi-flexible material such as a flextube, and the proximal section 136 may be formed from a rigid or semi-rigid material.

As shown in FIG. 6, the elongated tube 170 defines the longitudinal axis 110 of the inner blade shaft 100. In the illustrative embodiment, the elongated tube 170 is substantially straight. In other embodiments, the elongated tube 170 may define a curve or arc. In still other embodiments, one part of the tube 170 may be substantially straight and another part may define a curve or arc. For example, the part of the tube 170 may define an arc of approximately 60 degrees.

As described above, the inner blade shaft 100 includes a pair of cutting edges 106, 108, which are positioned in the distal section 176 of the tube 170. In the illustrative embodiment, the cutting edges 106, 108 are formed from the same metallic material as the rest of distal section 176. In other embodiments, the cutting edges 106, 108 may be formed from one material such as, for example, a stainless steel, and the rest of the distal section 176 (and elongated tube 170) may be formed from another material such as, for example, a polymeric material. The cylindrical outer surface 178 has a distal edge 180 that connects the proximal ends of the edges 106, 108, and the elongated tube 170 includes another edge 182 that connects the distal ends of the edges 106, 108. The edges 106, 108, 180, 182 cooperate to define a distal opening 184 in the elongated tube 170. The distal opening 184 is axially aligned with the cutting slot 16 when the blade shafts 100, 102 are assembled.

As shown in FIGS. 5-6, the distal opening 184 opens into the longitudinal passageway 104 of the inner blade shaft 100. The passageway 104 is defined by a cylindrical inner surface 186 and extends proximally to an opening 188 defined in the proximal end 174 of the elongated tube 170. The wall thickness defined between the inner surface 186 and the outer surface 178 is between about 0.100 and 0.130 millimeters and is sized to permit a larger diameter passageway 104.

The passageway 104 has a diameter 190 that is defined by the inner surface 186. The diameter 190 is in a range of about 1.8 millimeters to about 2.9 millimeters. In the illustrative embodiment, the diameter 190 is constant along the length of the passageway 104, but, in other embodiments, the diameter 190 may vary. For example, the diameter of the passageway in the distal section 176 of the tube 170 may be less than the diameter of the passageway in the proximal section 136. In that way, the diameter may be, for example, stepped or tapered along the length of the tube 170 to facilitate suction and reduce the possibility of clogging in certain applications. Additionally, in the illustrative embodiment, the inner surface 186 of the tube 170 is coated with a lubricious material such as, for example, a hydrophilic material, silicone, and so forth to reduce the possibility of clogging.

The outer blade shaft 102 of the blade assembly 14 includes an elongated tube 200 that extends from a distal end 202 to a proximal end 204. In the illustrative embodiment, the elongated tube 200 is formed from a bio-compatible metallic material such as, for example, stainless steel. The distal end 202 of the tube 200 is formed from a surgical steel such as, for example a high carbon steel or nickel alloy that is welded, press fit, or swaged to the proximal section of the tube 200. In that way, the distal end 202 is formed as a hardened steel tip of the tube 170. In the illustrative embodiment, the distal end 202 of the outer shaft 102 and the distal section 176 of the inner shaft are formed from different materials. It should be appreciated that in other embodiments the shafts 100, 102 may be formed from the same material.

In other embodiments, the tube 200 may be formed from a plastic or other rigid polymer. While the elongated tube 200 is illustratively formed separately in one or more pieces and later assembled, in other embodiments the tube 200 may be formed as a single, monolithic component and from the same material. In other embodiments, each of the pieces of the tube 200 may be formed from different materials or modified to possess different properties. For example, one section of the tube 200 may be made malleable or bendable while another section of the tube 200 remains rigid or semi-rigid. In that way, the malleable portion of the tube may be bent during surgery to provide the surgeon with improved access to the surgical area and returned to its original shape after surgery.

As shown in FIG. 6, the elongated tube 200 defines the longitudinal axis 206 of the outer blade shaft 102. In the illustrative embodiment, the elongated tube 200 is substantially straight. In other embodiments, the elongated tube 200 may define a curve or arc. In still other embodiments, one part of the tube 200 may be substantially straight and another part may define a curve or arc.

In the illustrative embodiment, the tube 200 has a constant outer diameter. In other embodiments, the tube 200 may include one or more stepped sections along its length. In still other embodiments, the tube 200 may taper along its length. In still other embodiments, the outer diameter of the proximal section may be smaller than the outer diameter of the distal section to, for example, accommodate a similarly configured inner blade shaft. In other embodiments, the distal section of the shaft 102 may have an outer diameter smaller than the outer diameter of proximal section to facilitate visualization of the surgical site.

The elongated tube 200 includes a cylindrical outer surface 208 that extends between the ends 202, 204. In the illustrative embodiment, the outer surface 208 is coated with a lubricious material such as, for example, a hydrophilic material, silicone, and so forth to reduce friction and facilitate movement of the shaft 102 within the nasal passage. In other embodiments, the tube 200 may also be coated with an anti-reflective material.

As described above, the outer blade shaft 102 includes the cutting slot 16, which is defined at the distal end 202 in the surface 208. The shaft 102 also has a pair of cutting edges 112, 114 that line the slot 16. In the illustrative embodiment, the cutting edges 112, 114 are formed from the same metallic material as the rest of distal end 202 of the tube 200. In other embodiments, the cutting edges 112, 114 may be formed from one material such as, for example, a stainless steel, and the rest of the distal end 202 (and elongated tube 200) may be formed from another material such as, for example, a polymeric material.

As shown in FIG. 6, the cylindrical outer surface 208 has a distal edge 210 that connects the proximal ends of the edges 112, 114. The elongated tube 200 also includes another edge 212 that connects the distal ends of the edges 112, 114. In the illustrative embodiment, the edges 112, 114, 210, 212 cooperate to define the cutting slot 16 in the elongated tube 200.

As shown in FIGS. 5-6, the cutting slot 16 opens into a longitudinal passageway 214 of the outer blade shaft 102. The passageway 214 is defined by a cylindrical inner surface 216 and extends proximally to an opening 218 defined in the proximal end 204 of the elongated tube 200. The wall thickness defined between the inner surface and the outer surface of the shaft 102 is sized to permit a larger diameter passageway and thereby a larger diameter inner blade shaft.

The passageway 214 has a distal diameter 220 that is defined by the inner surface 216. The diameter 220 is illustratively in a range of about 2.4 millimeters to about 3.5 millimeters. The passageway 214 has a proximal diameter 222 that is greater than the distal diameter 220. The diameter 222 is in a range of about 2.7 millimeters to about 3.8 millimeters. It should be appreciated that in other embodiments, the passageway 214 may have a constant diameter along its length.

As shown in FIG. 5, the inner blade shaft 100 is inserted into the passageway 214 of the outer blade shaft 102 when the blade assembly 14 is assembled. In the illustrative embodiment, the distal section 176 of the inner blade shaft 100 has a maximum outer diameter that substantially matches the inner distal diameter 220 of the outer blade shaft 102. The proximal section 136 of the inner blade shaft 100 has a maximum outer diameter that is less than the inner proximal diameter 222 of the outer blade shaft 102. In that way, a gap 224 is defined between proximal sections of the blade shafts 100, 102, while the matching diameters of the distal sections, in conjunction with the o-ring 162 at the distal end 202 of the outer shaft 102, center the inner blade shaft 100 in the passageway 214 such that longitudinal axes 110, 206 are co-linear.

As shown in FIG. 6, the outer surface 208 of the blade shaft 102 has an outer diameter 226. The diameter 226 is in a range of about 3.0 millimeters to about 4.0 millimeters. In the illustrative embodiment, the diameter 226 is constant along the length of the blade shaft 102, but, in other embodiments, the diameter 226 may vary. For example, the outer diameter of the blade shaft 102 at its distal end 202 may be less than its outer diameter at the proximal end 204. In that way, the diameter may be, for example, stepped or tapered along the length of the shaft.

Figure 7:
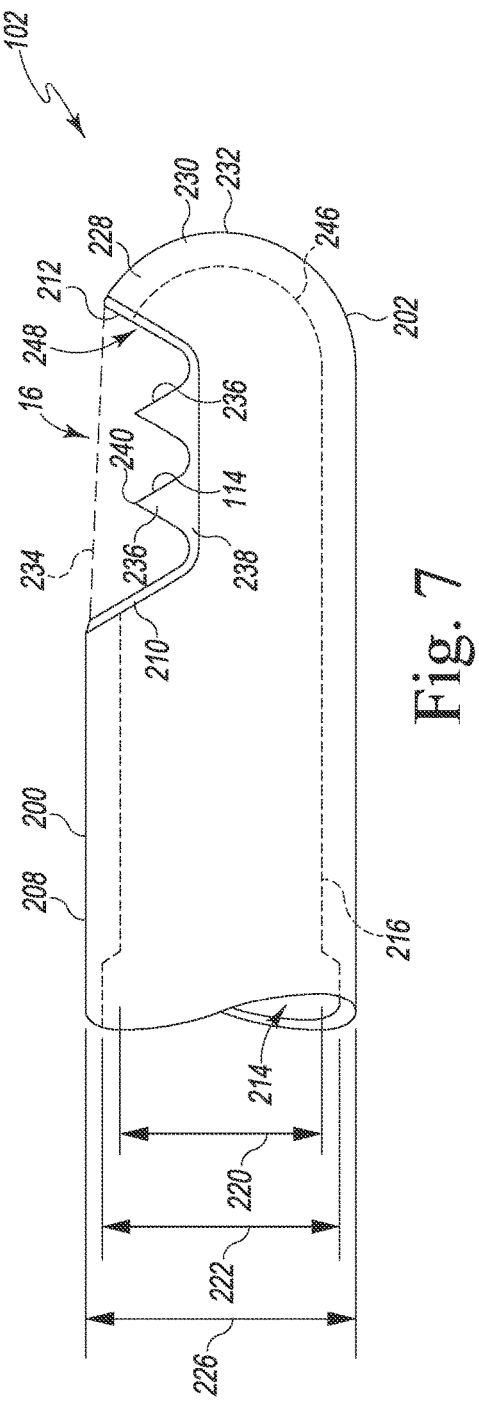
FIG. 7 is a side elevation view of the distal end of the outer blade shaft of the blade assembly of FIGS. 3-5.
Figure 8:
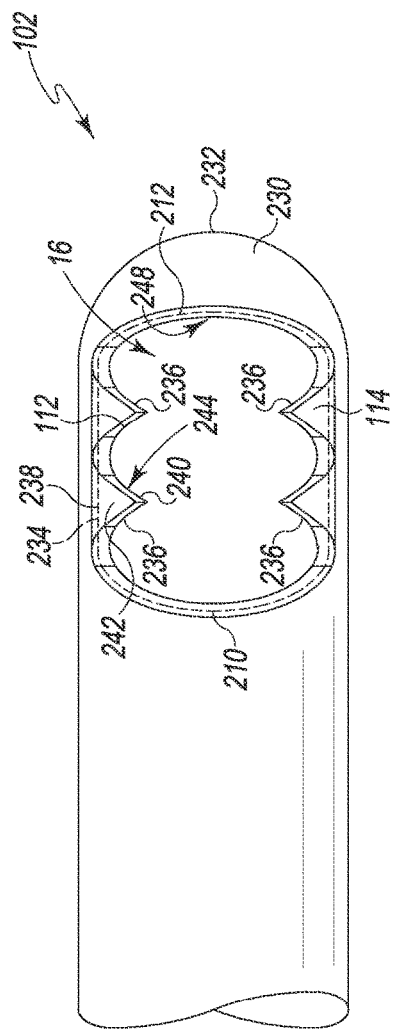
FIG. 8 is a top plan view of the distal end of the outer blade shaft of FIG. 7.

Referring now to FIGS. 7-8, the outer blade shaft 102 includes a closed distal tip 228. In other words, the longitudinal passageway 214 is not exposed or accessible through the tip 228 of the blade shaft 102 and access is permitted at the distal end 202 only through the cutting slot 16 in the surface 208. In that way, the distal tip 228 is an atraumatic tip that prevents or reduces damage to the anatomy caused by the distal end 18 of the blade assembly 14. In the illustrative embodiment, the distal tip 228 is defined by a rounded, convex surface 230 such that the tip 228 is bull-nosed. In the illustrative embodiment, the surface 230 is a spherical, but it should be appreciated that in other embodiments the surface 230 may take a rounded form other than spherical.

The rounded, convex surface 230 extends from an apex 232 to a proximal edge 212. As described above, the edge 212 cooperates with the edges 112, 114, 210 to define the cutting slot 16. As shown in FIGS. 7-8, each of the edges 112, 114, 210, 212 includes a chamfer or radius. The edge 210 and the edge 212 cooperate to define a curved imaginary plane 234 that defines the outer boundary of the cutting edges 112, 114. In that way, the edges 112, 114 are recessed and the blade shaft 102 has no sharp edges that extend beyond the outer surfaces 208, 230.

Each of the cutting edges 112, 114 of the shaft 102 is illustratively serrated, and each edge includes a pair of cutting teeth 236. In other embodiments, one or both of the cutting edges 112, 114 may include additional cutting teeth. In still other embodiments, one or both of the edges 112, 114 may include a single, continuous sharp edge. As shown in FIGS. 7-8, each tooth 236 extends from a base 238 to a tip 240 positioned within the boundary defined by the curved imaginary plane 234. Each tooth 236 is illustratively angled approximately 50 degrees relative to horizontal.

Each tooth 236 also includes a substantially planar outer surface 242 extending between the tip 240 and the base 238. As shown in FIG. 7, the teeth 236 are equal in length. In other embodiments, the one or more teeth may extend different lengths. Each tooth 236 also includes a concave curved inner surface 244 (see FIGS. 12-13) that substantially matches the cylindrical inner surface 216 of the outer blade shaft 102.

As shown in FIG. 7, the cylindrical inner surface 216 is connected to a rounded, concave inner surface 246, which defines a chamber 248 at the distal end of the longitudinal passageway 214. In the illustrative embodiment, the inner surface 246 has a shape that corresponds to the shape of the outer rounded, convex surface 230 that defines the distal tip 228. In other embodiments, the distal end of the passageway 214 may be defined by a flat planar surface extending inward from the cutting slot 16.

Figure 9:
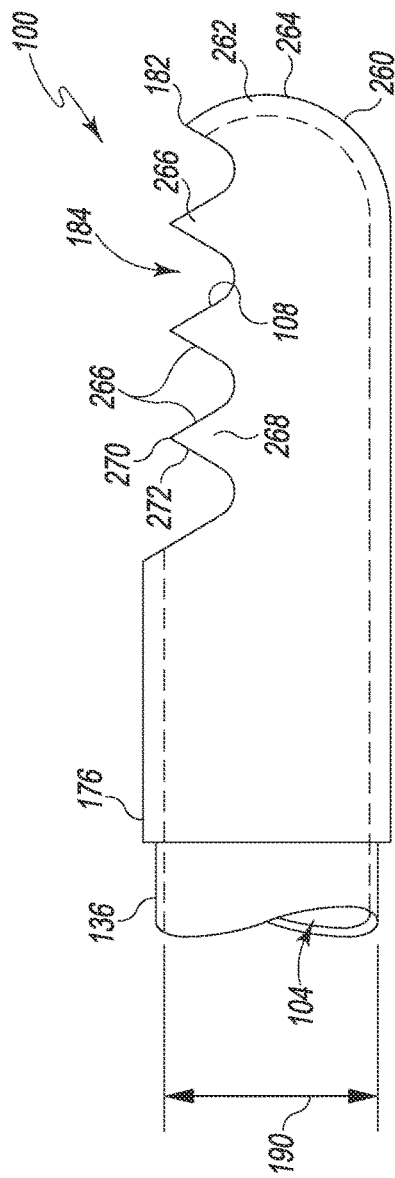
FIG. 9 is a side elevation view of the distal end of the inner shaft of the blade assembly of FIGS. 3-5.
Figure 10:
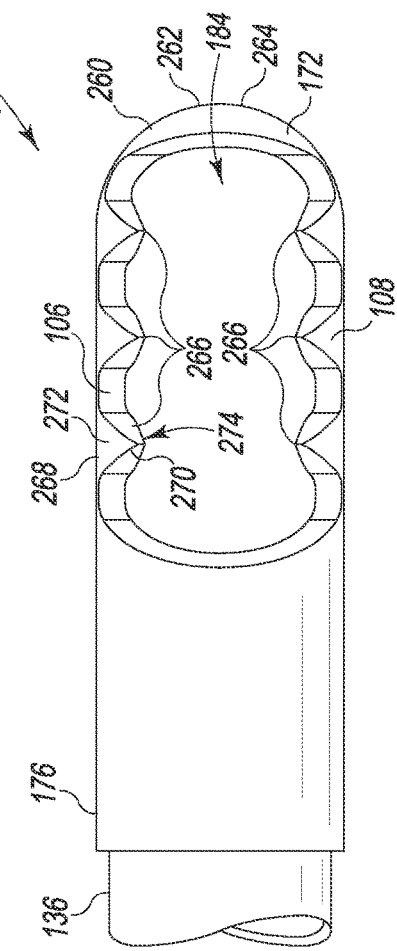
FIG. 10 is a top plan view of the distal end of the inner blade shaft of FIG. 9.

Referring now to FIGS. 9-10, the inner blade shaft 100 includes a closed distal tip 260 that is received in the chamber 248 defined in the outer blade shaft 102. In the illustrative embodiment, the distal tip 260 is defined by a rounded, convex surface 262 that matches the shape and configuration of the rounded, concave inner surface 246 of the outer blade shaft 102. In the illustrative embodiment, the surface 262 is a spherical, but it should be appreciated that in other embodiments the surface 262 may take a rounded form other than spherical.

The rounded, convex surface 262 extends from an apex 264 to a proximal edge 182. As described above, the edge 182 cooperates with the edges 106, 108, 180 to define the distal opening 184 of the inner blade shaft 100. In the illustrative embodiment, the area of the distal opening is approximately two-thirds of the cross-sectional area of the longitudinal passageway 104.

Each of the cutting edges 106, 108 of the shaft 100 is illustratively serrated, and each edge includes a number of cutting teeth 266. In other embodiments, one or both of the cutting edges 106, 108 may include additional cutting teeth. In still other embodiments, one or both of the edges 106, 108 may include a single, continuous sharp edge. As shown in FIGS. 9-10, each tooth 266 extends from a base 268 to a tip 270.

Each tooth 266 also includes a curved outer surface 272 extending between the tip 240 and the base 238. The outer surfaces 272 substantially match inner surfaces 244 of the teeth 236 of the outer blade shaft 102. As shown in FIG. 9, the teeth 266 are equal in length. In other embodiments, the one or more teeth may extend different lengths. Each tooth 266 also includes a substantially planar inner surface 274 (see FIGS. 12-13).

As described above in regard to FIG. 3, the cutting edges 106, 108 of the inner blade shaft 100 cooperate with the cutting edges 112, 114 to cut the tissue of a patient. In the illustrative embodiment, the cutting teeth 266 of the inner blade shaft 100 are offset from the cutting teeth 236 of the outer blade shaft 102, as shown in FIG. 3. In that way, the teeth 236, 266 form a common cutting edge on each side of the slot 16 when the inner blade shaft 100 is rotated relative to the outer blade shaft 102.

Figure 11:
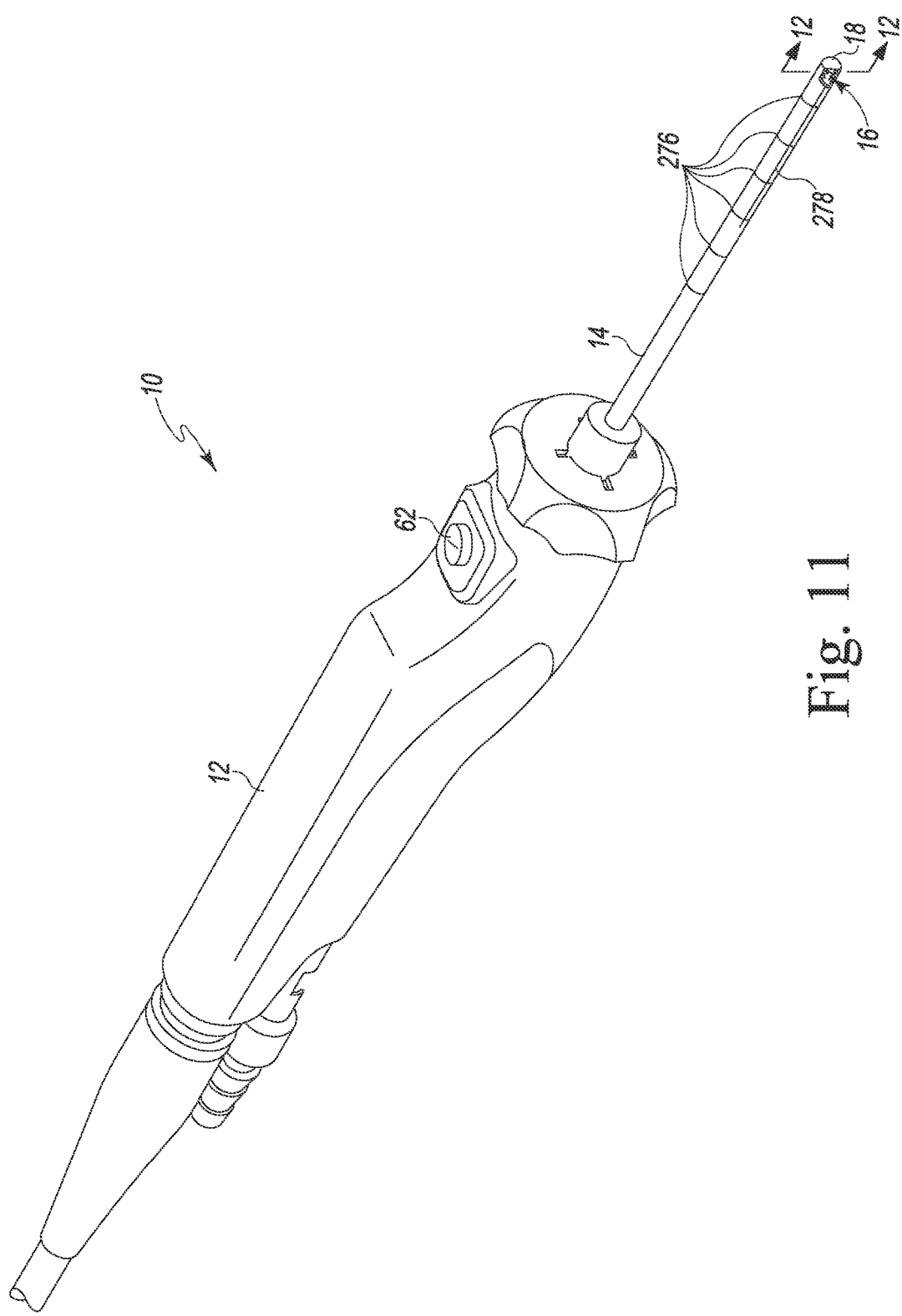
FIG. 11 is a perspective view of the surgical instrument of FIG. 1 when assembled.

Referring now to FIG. 11, a blade assembly 14 may be attached to hand piece 12 in preparation for surgery. To do so, the proximal end 34 of the blade assembly 14 is aligned with the aperture 30 defined in the distal end 32 of the hand piece 12. The blade assembly 14 is then advanced into the aperture 30. As the blade assembly 14 is moved along the aperture 30, the inner hub 120 is moved through the passageway 78 defined in the mounting collar 72. The blade assembly 14 may be rotated to align the splines 88 of the inner hub 120 with the slots defined in the splined surface 82 of the inner collar 80.

The blade assembly 14 may be advanced further into the aperture 30 to engage the splines 88 with the splined surface 82, thereby connecting the inner collar 80 with the hub 120. As the blade assembly 14 is advanced further into the aperture 30, the splines 76 of the outer hub 122 engage the splined surface 74 of the mounting collar 72, thereby fixing the outer hub 122 (and hence the outer blade shaft 102) in position relative to the hand piece 12. When the blade assembly 14 is properly positioned, the o-ring 132 attached to the inner hub 120 is engaged with the splined surface 82, and the proximal opening 188 of the inner blade shaft 100 is fluidly connected with the passageway 84 of the collar 80 and the passageway 96.

Prior to performing the surgery, the connector cable 38 of the hand piece 12 may be coupled to the connector 44 of the electrical cable 52 to supply electrical power to the motor 66. Additionally, the connector 36 of the hand piece 12 may be coupled to the connector 42, thereby connecting the vacuum pump 48 to the hand piece 12.

In a nasal polyp surgery, an endoscope may be advanced into the nasal passage of a patient to provide a view of the surgical area. The distal end 18 of the blade assembly 14 may be advanced into the nasal passage with the endoscope. In the illustrative embodiment, the closed distal tip 228 and the recessed cutting edges 112, 114 reduce the possibility of inadvertently nicking or cutting tissue or bone during insertion of the device.

The outer blade shaft 102 may include a number of markings 276 defined on its outer surface 208, as shown FIG. 11, which the surgeon may use to monitor the depth of the blade assembly 14. The outer blade shaft 102 may also include one or more marking 278, which indicate the orientation of the cutting slot 16 within the nasal passage. It should be appreciated that the marking 278 may also be used to monitor the depth of the blade assembly 14. In the illustrative embodiment, the markings 276, 278 are laser marked on the shaft 102. In other embodiments, other methods, such as, for example, printing, may be used to affix the markings 276, 278 on the shaft 102. It should also be appreciated that the markings may be made fluorescent or visible in darkness.

The surgeon may toggle or press the control button 62 on the hand piece 12 to energize the motor 66. The surgeon may also separately activate the vacuum pump 48. When the motor 66 is energized, the motor 66 causes the output shaft 92 to rotate clockwise and counterclockwise. It should be appreciated that the motor 66 may operate a single, continuous speed or at a variable speed.

The rotation of the shaft 92 is transmitted to the inner collar 80 via the gear assembly 90, thereby causing the inner collar 80. The splined connection between the inner collar 80 and inner hub 120 of the blade assembly 14 causes the inner hub 120 (and hence the inner blade shaft 100) to rotate. The hand piece 12 is configured to oscillate the direction of the motor 66 such that the inner blade shaft 100 oscillates clockwise and counter clockwise about its longitudinal axis to cut the tissue. It should be appreciated that the hand piece 12 may also be configured to rotate the motor 66 continuously in either direction.

Figure 12:
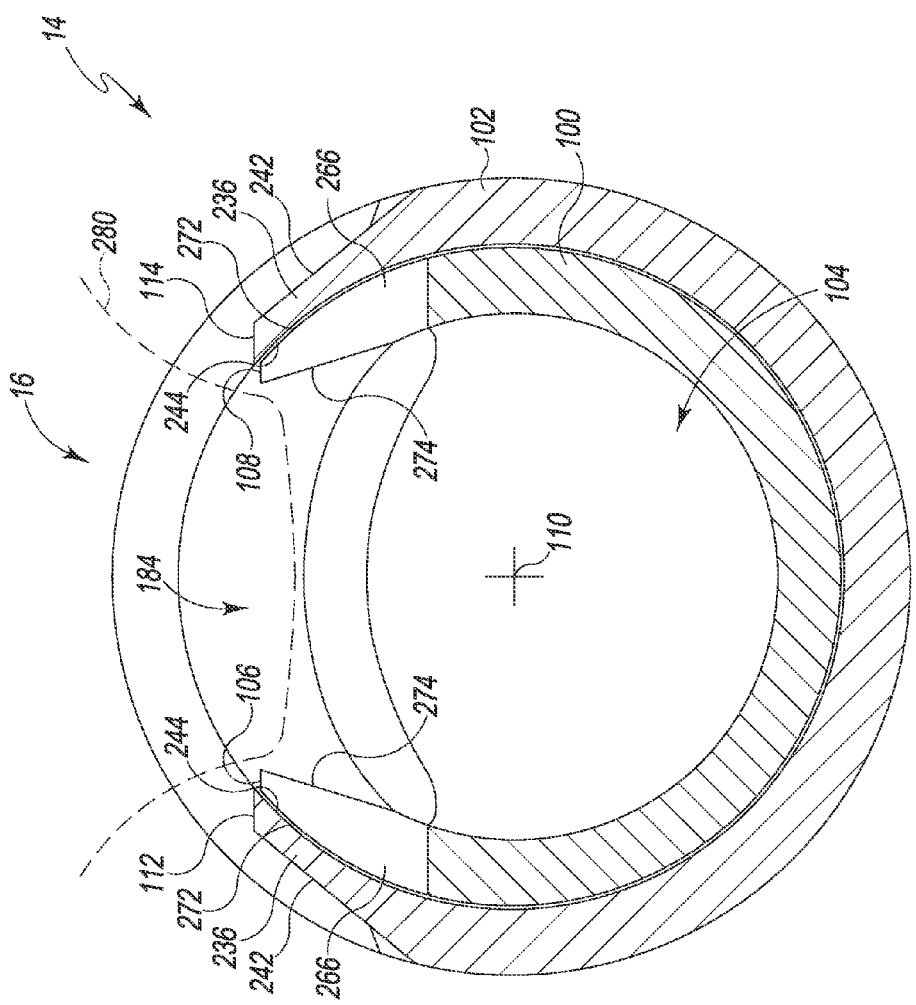
FIG. 12 is a cross-sectional elevation view of the distal end of the blade assembly taken along the line 12-12 in FIG. 11.

To remove tissue, the distal end 18 of the blade assembly 14 is advanced into contact with the target tissue 280. As described above, tissue is prevented from entering the passageway 104 by the closed distal tip 228 of the outer blade shaft 102. Instead, as shown in FIG. 12, the tissue must be advanced into the cutting slot 16. As the inner blade shaft 100 is rotated about its axis 110 by the motor 66, the cutting edge 106, for example, is advanced into engagement with the tissue 280.

The movement of the inner blade shaft 100 in one direction presses the tissue 280 into engagement with the cutting edges 108, 114. The serrated teeth 266 of the inner blade shaft 100 and the serrated teeth 236 of the outer blade shaft 102 cooperate to slice the target tissue 280. When the motor 66 reverses direction, the tissue 280 is pressed into engagement with the opposite cutting edges 106, 112. The serrated teeth 266 of the inner blade shaft 100 and the serrated teeth 236 of the outer blade shaft 102 then cooperate to slice the target tissue 280. As the instrument 10 is cutting the tissue, the closed distal tip 228 and the recessed cutting edges 112, 114 reduce the possibility of inadvertently cutting bone or overcutting the tissue.

Figure 13:
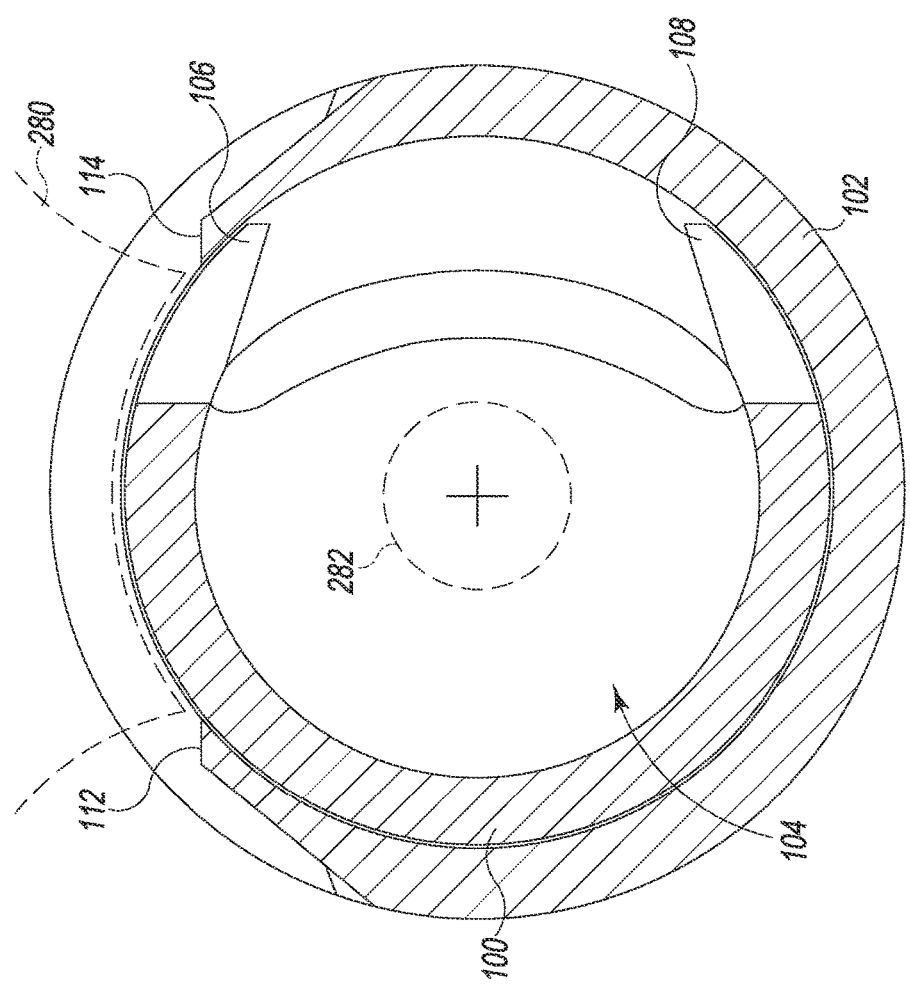
FIG. 13 is a view similar to FIG. 12 showing the inner blade shaft rotated relative to the outer shaft.

As shown in FIG. 13, the severed portion 282 of the tissue is drawn into the passageway 104 through the opening 184. When the vacuum pump 48 is activated, a suction air flow is created through the surgical instrument 10. When the blade assembly 14 is attached to the hand piece 12, the longitudinal passageway 104 of the inner blade shaft 100 is fluidly connected to the vacuum pump 48 via the hose 46, the connectors 36, 42, and the passageways 84, 96. As a result, the severed tissue 282 or other particles entering the passageway 104 of the inner blade shaft 100 are drawn out of the surgical instrument 10.

At the conclusion of surgery, the blade assembly 14 may be detached from the hand piece 12. The hand piece 12 may be cleaned and reused. Similarly, the blade assembly 14 may be cleaned and reused or, alternatively, disposed of. New or other blade assembly configurations may be used in future surgeries.

Figure 14:
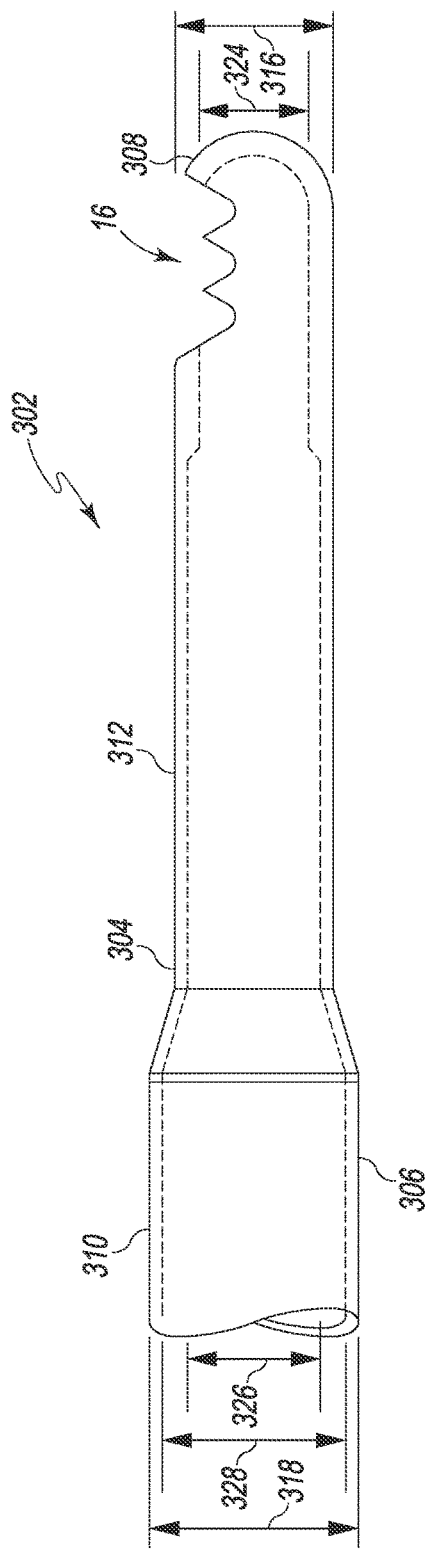
FIG. 14 is a side elevation view of another embodiment of an outer blade shaft for use in the blade assembly of FIG. 3.
Figure 15:
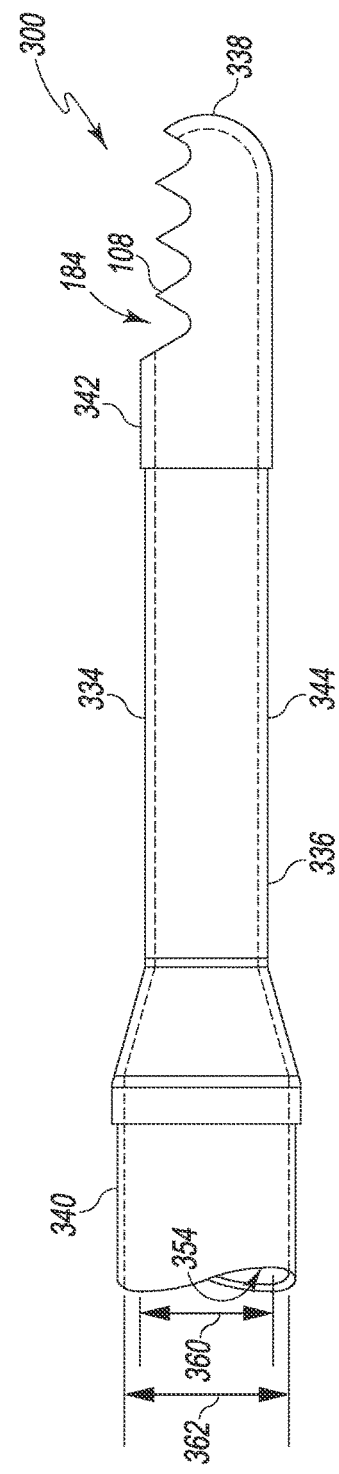
FIG. 15 is a side elevation view of another embodiment of an inner blade shaft for use with the outer shaft of FIG. 14.

The blade assembly 14 may be interchangeable with alternative blade assemblies including blade shafts of different configurations. For example, another combination of inner and outer blade shafts (hereinafter inner blade shaft 300 and outer blade shaft 302) is shown in FIGS. 14-15. As shown in FIG. 14, the outer blade shaft 302 includes an elongated tube 304 with a stepped outer surface 306. Like the elongated tube 200, the elongated tube 304 extends from a distal end 308 to a proximal end (not shown). In the illustrative embodiment, the elongated tube 304 is formed from a metallic material such as, for example, stainless steel.

The tube 304 includes a cylindrical proximal section 310 and a distal section 312. The distal section 312 includes a cylindrical outer surface 314, which has an outer diameter 316 that is smaller than the outer diameter 318 of the proximal section 310. In the illustrative embodiment, the outer diameter 316 of the distal section 312 is about 3 millimeters, and the outer diameter 318 of the proximal section 310 is about 4 millimeters. Additionally, the distal section 312 extends between about 18 and about 19 millimeters. In still other embodiments, the outer diameter of the proximal section may be smaller than the outer diameter of the distal section to, for example, facilitate suction and reduce the possibility of clogging in certain applications.

The sections 310, 312 are formed separately from the same metallic material and later assembled by welding, press fit, or swaging. In other embodiments, the sections 310, 312 may be formed as a single, monolithic component or the shaft 102 may be formed from additional pieces that are later assembled. Additionally, the sections 310, 312 may be formed from different materials. For example, the distal section 312 may be formed from as a malleable or bendable section, and the proximal section 310 may be formed from a rigid or semi-rigid material.

The configuration of the cutting slot 16 of the outer blade shaft 302 is identical to the cutting slot described above in regard to FIGS. 1-13. As shown in FIG. 14, the cutting slot 16 opens into a longitudinal passageway 320 of the outer blade shaft 102. The passageway 320 is defined by a cylindrical inner surface 322 and extends proximally to an opening (not shown) defined in the proximal end of the elongated tube 304. The passageway 320 has a distal diameter 324 that is defined by the inner surface 216. The diameter 324 is illustratively is equal to about 2.4 millimeters. The passageway 320 has an intermediate diameter 326 that is equal to about 2.7 millimeters. A third diameter 328 is defined in the proximal section 310 and is equal to about 3.8 millimeters.

Like the shaft 102, the outer blade shaft 302 includes a closed distal tip 330. The longitudinal passageway 320 is therefore not exposed or accessible through the tip 330 of the blade shaft 302 and access is permitted at the distal end 308 only through the cutting slot 16 in the outer surface 306.

As described above, the outer blade shaft 302 may be combined with an inner blade shaft 300. As shown in FIG. 15, the inner blade shaft 300 includes an elongated tube 334 with a stepped outer surface 336. Like the elongated tube 170 of the shaft 100, the elongated tube 334 extends from a distal end 338 to a proximal end (not shown). In the illustrative embodiment, the elongated tube 334 is formed from a metallic material such as, for example, stainless steel.

The tube 334 includes a cylindrical proximal section 340, a distal section 342, and an intermediate section 344. The distal section 342 includes a cylindrical outer surface 346, which has an outer diameter that is smaller than the outer diameter of the proximal section 340 but larger than the outer diameter of the intermediate section 344. The sections 340, 342, 344 are formed separately from the same metallic material and later assembled by welding, press fit, or swaging. In other embodiments, the sections 340, 342, 344 may be formed as a single, monolithic component or the shaft 300 may be formed from additional pieces that are later assembled. Additionally, the sections 340, 342, 344 may be formed from different materials. For example, the sections 340, 342 may be formed from a flexible or semi-flexible material such as a flextube, and the proximal section 340 may be formed from a rigid or semi-rigid material.

As shown in FIG. 15, the configuration of the cutting edges 106, 108 and the distal opening 184 of the shaft 300 is identical to the configuration the cutting edges 106, 108 and the distal opening 184. The distal opening 184 opens into the longitudinal passageway 354 of the inner blade shaft 300. The passageway 354 is defined by a stepped cylindrical inner surface 356 and extends proximally to an opening (not shown) defined in the proximal end of the elongated tube 334. The passageway 354 has a distal diameter 360 that is equal to about 1.8 millimeters. The passageway 354 then expands to a proximal diameter 362 of about 2.9 millimeters in the proximal section 340.

Like the blade assembly 14, the inner blade shaft 300 may be secured to an inner hub 120 such that the blade shaft 300 may be rotated relative to the outer blade shaft 302. Similarly, the outer blade shaft 302 may be secured to an outer hub 122 to form a blade assembly that is interchangeable with the blade assembly 14. In use, the stepped passageway 354 of the inner blade shaft 300 creates a nozzle effect that improves the suction within the passageway 354 and reduces the possibility of clogging.

Figure 16:
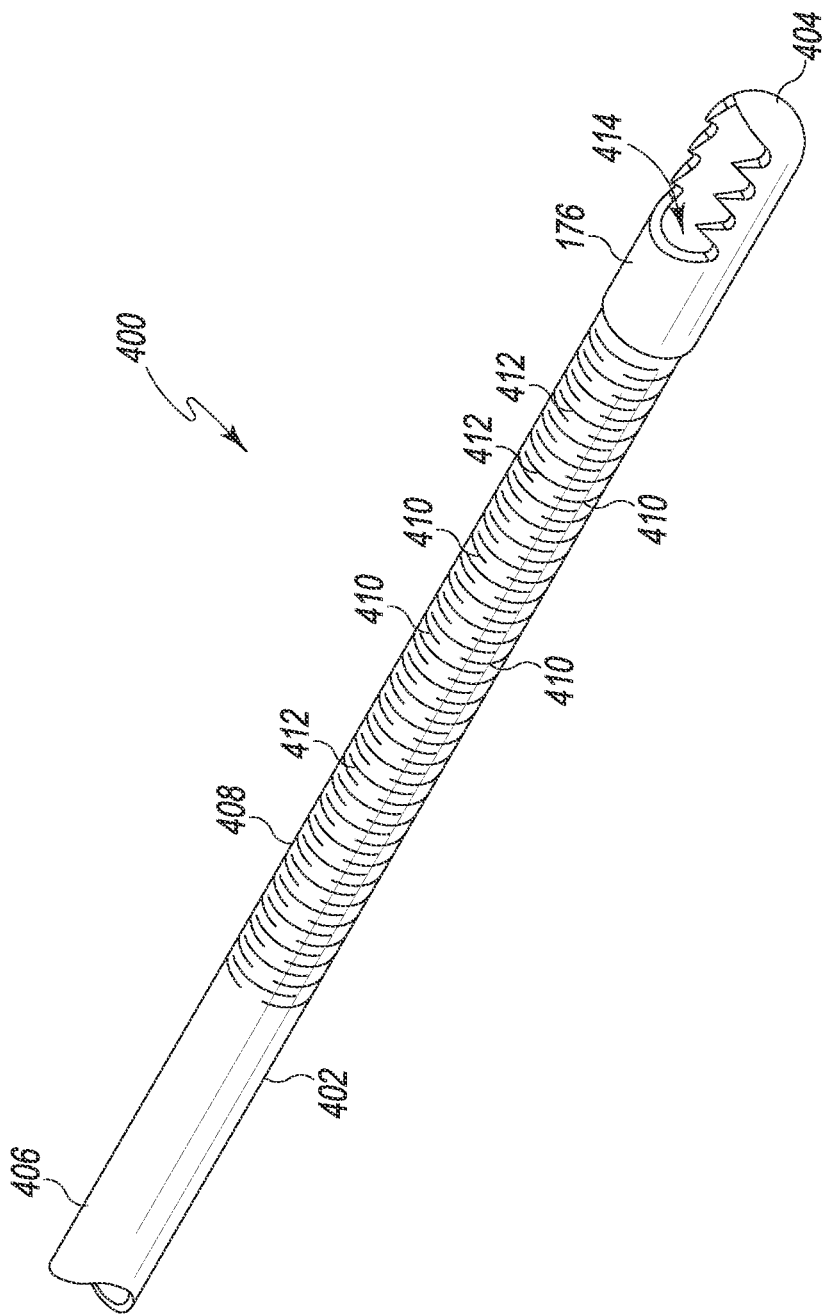
FIG. 16 is a perspective view of another embodiment of an inner blade shaft.

As described above, the blade assembly 14 may include an inner blade shaft (hereinafter inner blade shaft 400) that includes a flexible or semiflexible section near its distal end. Referring now to FIG. 16, the inner blade shaft 400 includes an elongated tube 402 that extends from a distal end 404 to a proximal end (not shown). In the illustrative embodiment, the elongated tube 402 is formed from a metallic material such as, for example, stainless steel.

The tube 402 includes a distal section 176, a cylindrical proximal section 406, and an intermediate section 408. The distal section 176 has an identical configuration to the distal section 176 of the inner blade shaft 100. The intermediate section 408 includes a plurality of circumferential slots or openings 410, which divide the section 408 into segments 412 and permit the intermediate section 408 to flex and bend. In the illustrative embodiment, the section 408 extends between about 2.0 and about 4.0 millimeters. The proximal section 406 is formed as a rigid or semi-rigid component. The sections 176, 406, 408 are formed separately from the same metallic material and later assembled by welding, press fit, or swaging. In other embodiments, the sections 176, 406, 408 may be formed from different materials, including, for example, polymeric materials.

As shown in FIG. 16, the shaft 400 includes a longitudinal passageway 414 similar to the longitudinal passageway 104 of the shaft 100. To maintain the rate of suction in the inner blade shaft 400, the passageway 414 may be encased by, for example, a polymer coating or tubing to seal the circumferential openings 410 of the intermediate section 408.

In the illustrative embodiment, the passageway 414 has a constant diameter. In other embodiments, the passageway 414 and hence the tube 200 may include one or more stepped sections along its length. In still other embodiments, the tube 402 may taper along its length. In still other embodiments, the outer and inner diameters of the proximal section may be smaller than the outer and inner diameters of the distal section to, for example, facilitate suction and reduce the possibility of clogging in certain applications. In other embodiments, the distal section of the tube 402 may have outer and inner diameters smaller than the outer and inner diameters of proximal section to facilitate visualization of the surgical site and reduce the possibility of clogging in certain applications.

Figure 17:
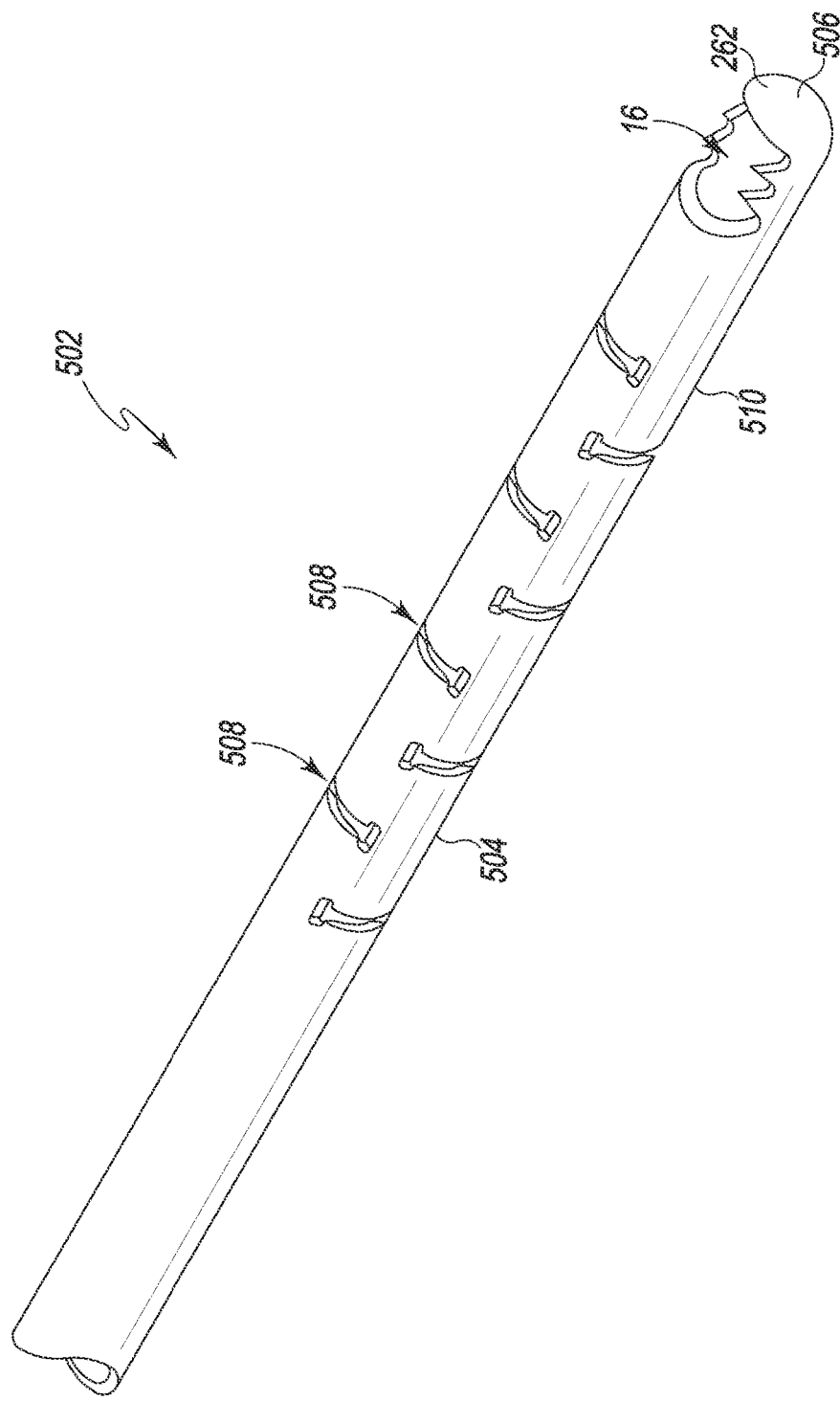
FIG. 17 is a perspective view of another embodiment of an outer blade shaft.

As described above, the inner blade shaft 400 may be used in conjunction with an outer blade shaft (hereinafter outer blade shaft 502) that includes a malleable or bendable section near its distal end. Referring now to FIG. 17, the outer blade shaft 502 includes an elongated tube 504 that extends from a distal end 506 to a proximal end (not shown). In the illustrative embodiment, the elongated tube 504 is formed from a metallic material such as, for example, stainless steel.

The elongated tube 504 has a plurality of circumferential slots 508 positioned proximal of the cutting slot 16. The slots 508 are sized and spaced to make the distal section 510 of the tube 504 bendable or malleable to permit the surgeon greater flexibility in positioning the blade assembly during surgery. The distal section 510 is configured to return to its substantially straight configuration following surgery. In the illustrative embodiment, the distal section 510 extends between about 2.0 and about 4.0 millimeters. It should be appreciated that the other aspects of the outer blade shaft 502 are substantially similar to the outer blade shaft 102 described above, including, for example, the closed distal tip 228 and the cutting slot 16.

The shaft 502 includes a passageway sized to receive the inner blade shaft 400. The passageway illustratively has a constant diameter. In other embodiments, the passageway 414 and hence the tube 504 may include one or more stepped sections along its length. In still other embodiments, the tube 504 may taper along its length. In still other embodiments, the outer and inner diameters of the proximal section may be smaller than the outer and inner diameters of the distal section to accommodate a similarly configured inner blade shaft. In other embodiments, the distal section of the tube 504 may have outer and inner diameters smaller than the outer and inner diameters of proximal section to facilitate visualization of the surgical site.

Figure 18:
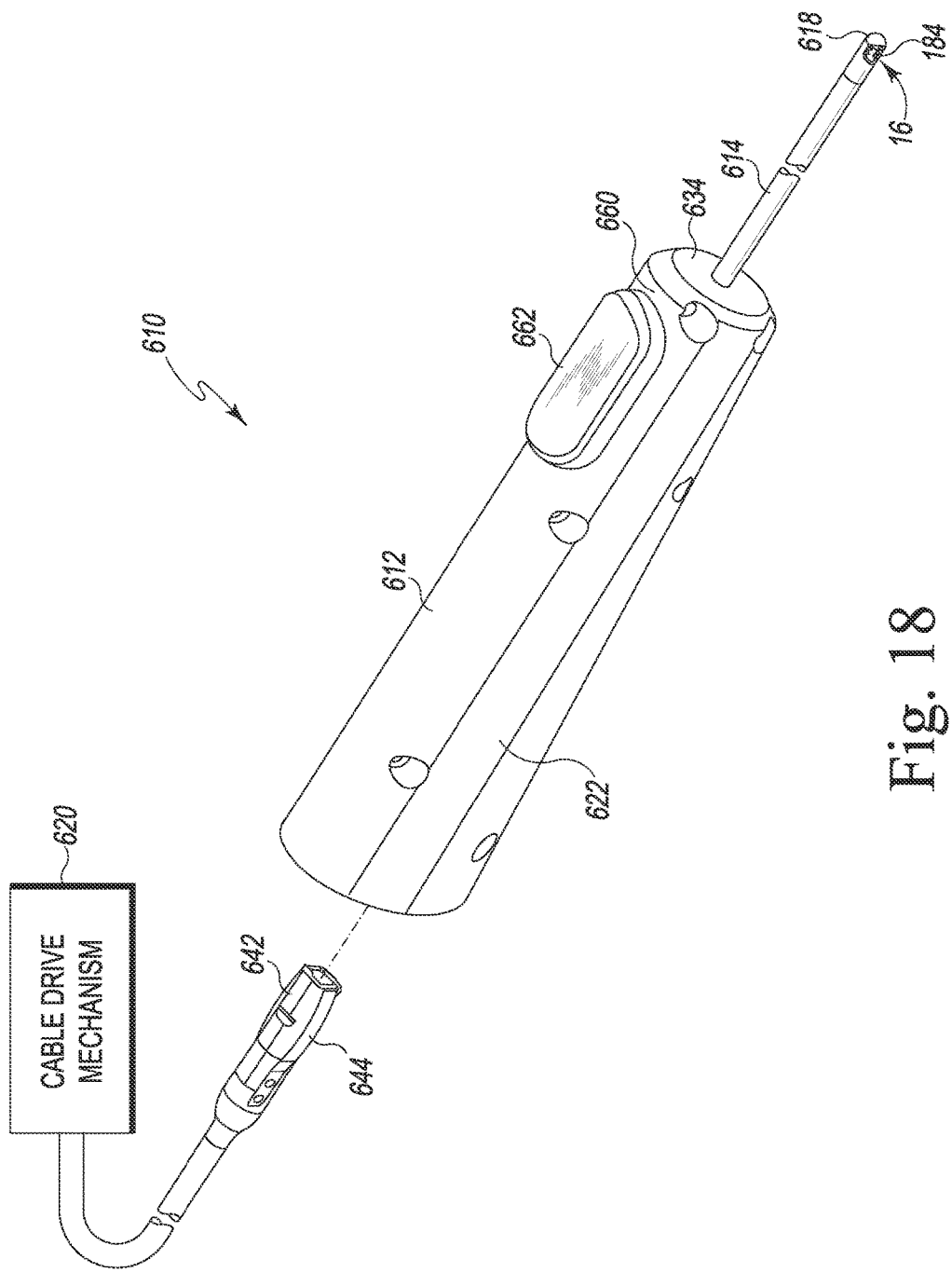
FIG. 18 is an exploded perspective view of another embodiment of a surgical instrument for use in surgeries to treat disorders of the ear, nose, and throat.
Figure 19:
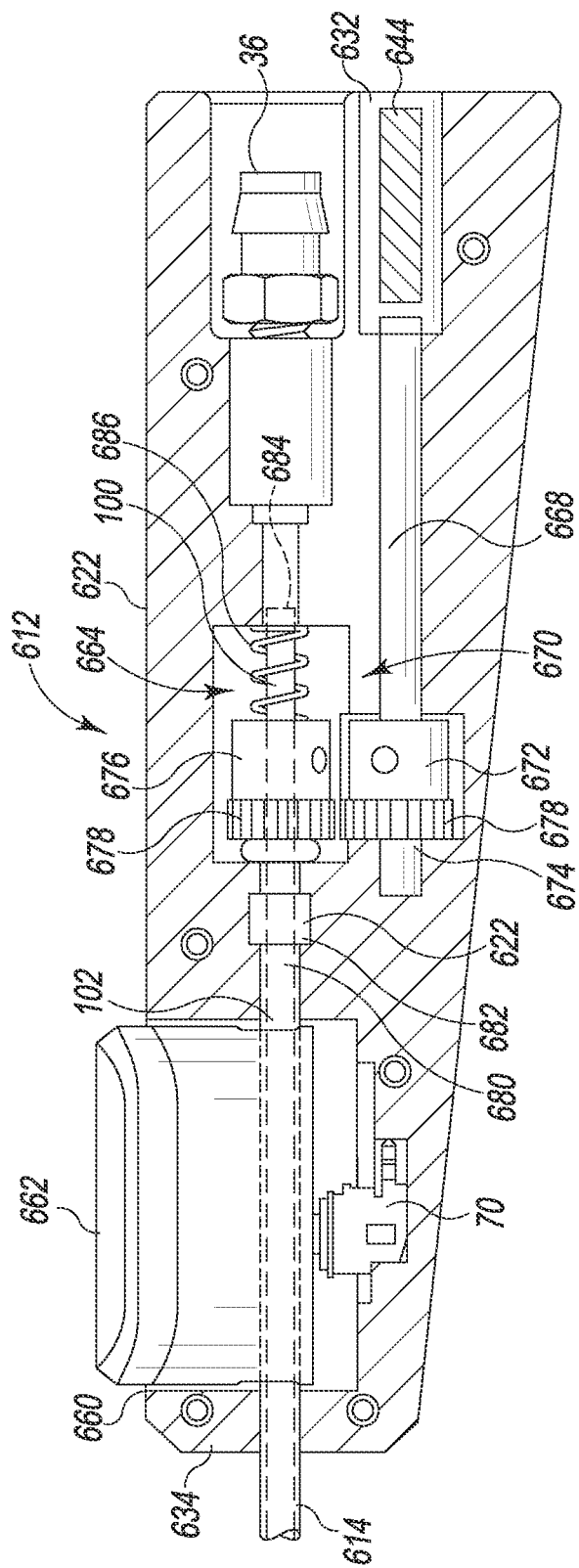
FIG. 19 is a partial cross-sectional elevation diagrammatic view of a hand piece of the surgical instrument of FIG. 18.

Referring now to FIGS. 18-19, another embodiment of a surgical instrument (hereinafter surgical instrument 610) is shown. Some of the features of the embodiment of FIGS.

18-19 are similar to the embodiment described above. For such features, the references numbers from the embodiment described above will be used to identify those features in FIGS. 18-19. As shown in FIG. 18, the instrument 610 includes a hand piece 612 and a blade assembly 614 that extends outwardly from the hand piece 612 to a distal end 618. In the illustrative embodiment, the blade assembly 614 is secured to the hand piece 612 and not configured to be detached. Additionally, the instrument 610 is configured to be disposed after a single use.

A cutting slot 16 is positioned at the distal end 618 of the blade assembly 614. This embodiment of the surgical instrument is configured to be used with a cable drive mechanism 620, which may be included in a portable surgical console. The cable drive mechanism 620 is used to operate the blade assembly 620 to shave or cut tissue within the cutting slot 16. The surgical instrument 610 is also configured to be coupled to a negative pressure source such as a vacuum pump 48 to evacuate the severed tissue from the instrument 610.

The hand piece 612 of the surgical instrument 610 includes an elongated body 622. The body 622 is configured to be grasped by a user during operation of the surgical instrument 610. The elongated body 622 may be formed from a plastic, rigid polymer, or other rigid materials.

As shown in FIG. 19, the blade assembly 614 extends outwardly from a longitudinal end 632 of the body 622. The hand piece 612 also includes a connector 36 and a connector 638, which are positioned at the opposite longitudinal end 640 of the body 622. The connector 36 is configured to engage a hose connector 42 of the vacuum pump 48 such that the hand piece 612 (and hence the blade assembly 614) may be connected to the vacuum pump 48.

The connector 638 is configured to engage a connector 642 of the cable drive mechanism 620. One such mechanism uses the bi-plex or tri-plex coil drive cables commercially available from Heraeus Medical Components. The connectors 638, 642 also includes a pair of electrical contacts 644, which permit the user to activate the cable drive mechanism 620 using the hand piece 612.

As shown in FIGS. 18-19, the hand piece 612 also includes a control panel 660 positioned on the elongated body 622. In the illustrative embodiment, the control panel 660 includes a single control button 662, which may be toggled to activate the cable drive mechanism 620. In this embodiment, the vacuum pump 48 may be activated using a foot pedal or switch located on the pump 48. In other embodiments, the hand piece 612 may include additional controls such as toggles, levers, or other buttons. It should also be appreciated that in other embodiments the control panel 660 may be omitted from the hand piece 612, and the cable drive mechanism 620 and the pump 48 may be activated using a foot pedal or other control device.

As shown in FIG. 19, the hand piece 612 includes an electrical contact switch 70 that is positioned in an inner chamber 664 of the elongated body 622. When the button 662 is toggled or pressed by the user, the switch 70 is configured to generate an electrical output. The electrical output is relayed to the cable drive mechanism 620 via the contacts 644 and the connectors 638, 642.

The hand piece 612 also includes an input shaft 668 that is positioned in the inner chamber 664. The input shaft 668 is configured to engage the connector 642 of the cable drive mechanism 620 within the connector 638. When the cable drive mechanism 620 is activated, the connector 642 causes the input shaft 668 to rotate. The rotation of the input shaft 668 is transmitted to the blade assembly 614 via a gear assembly 670.

As shown in FIG. 19, the gear assembly 670 includes an input gear 672 mounted to a distal end 674 of the input shaft 668. The gear assembly 670 also includes an output gear 676 mounted to an inner blade shaft 100 of the blade assembly 614. Each of the gears 672, 676 is press fit onto its respective shaft 668, 100 and includes a number of teeth 678. The teeth 678 of the gears 672, 676 are intermeshed such that rotation of the gear 672 causes rotation of the gear 676 (and hence inner blade shaft 100). Each of the gears 672, 676 and the input shaft 668 may be formed from a rigid polymeric material or a metallic material such as, for example, stainless steel.

The blade assembly 614 includes the inner blade shaft 100 and an outer blade shaft 102 that is secured to the hand piece 612. In the illustrative embodiment, a proximal end 680 of the outer blade shaft 102 is press fit into a collar 682 secured to the elongated body 622 of the hand piece 612. Similar to the embodiment described above, the inner blade shaft 100 extends outwardly from the proximal end 680 of the shaft 102 to a proximal end 684 that is fluidly coupled to the vacuum hose connector 36. In that way, negative pressure may be created through the longitudinal passageway 104 to draw severed tissue from the distal end 618 of the blade assembly 614, through the hand piece 612, and out of the instrument 610.

In the illustrative embodiment, the hand piece 612 also includes a biasing element such as, for example, a spring 686 that is engages the output gear 676. The spring 686 biases the output gear 676 (and hence the inner blade shaft 100) in a distal direction such that axial alignment between the distal opening 184 of the inner blade shaft 100 and the cutting slot 16 is maintained.

In use, the cable drive mechanism 620 and the vacuum pump 48 are activated as described above. The input shaft 668 is rotated by the cable drive mechanism 620. The rotation of the input shaft 668 causes rotation of the gears 672, 676 and hence the inner blade shaft 100. Tissue positioned in the cutting slot 16 may be cut or severed by the two or more the cutting edges 106, 108, 112, 114 of the shafts 100, 102. The severed tissue may be withdrawn from the blade assembly 614 and the instrument 610 via suction created by the vacuum pump 48.

While the embodiment of FIGS. 18-19 is shown with the inner blade shaft 100 and the outer blade shaft 102, it should be appreciated that any of the blade shaft designs described herein may be used with a cable-driven design, including, for example, the stepped blade shaft, flexible, and malleable designs. It should also be appreciated that the cable-drive mechanism may be incorporated into a reusable instrument and/or an instrument designed to use interchangeable blade assemblies.

Figure 20:
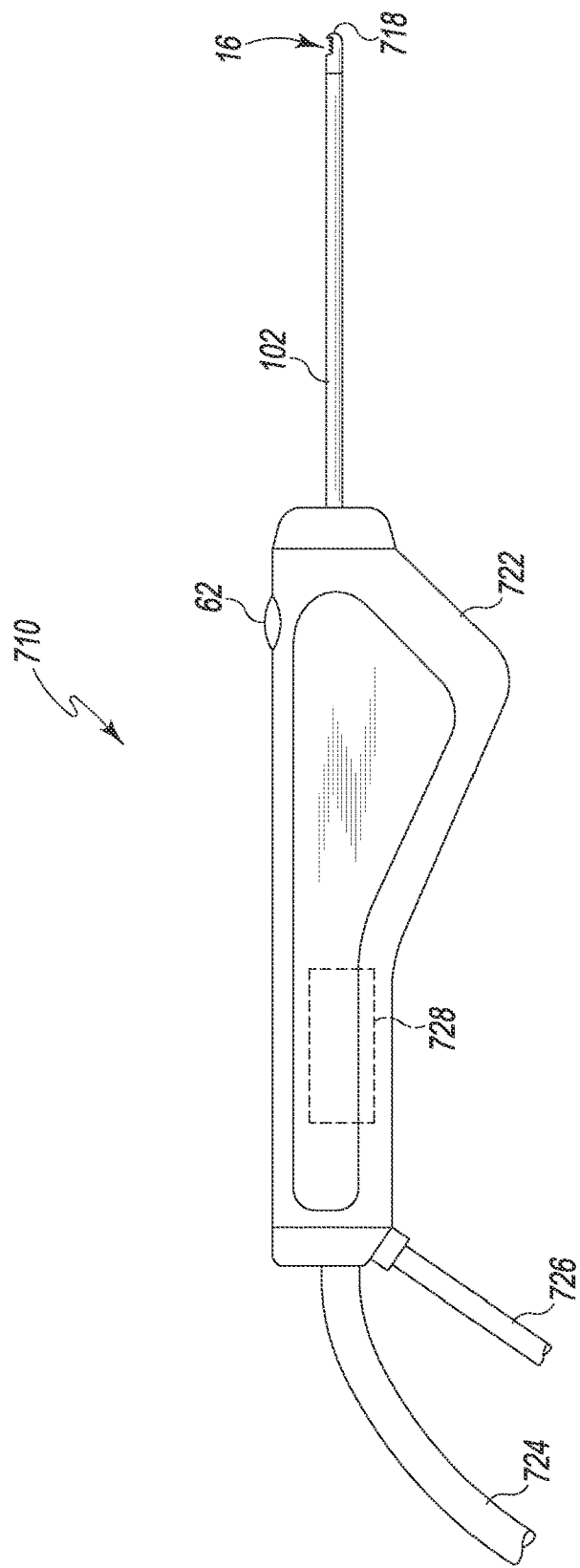
FIG. 20 is a perspective view of another embodiment of a surgical instrument for use in surgeries to treat disorders of the ear, nose, and throat.

Referring now to FIG. 20, another embodiment of a surgical instrument (hereinafter instrument 710) is shown. Some of the features of the embodiment of FIG. 20 are similar to the embodiments described above. For such features, the references numbers from the embodiments described above will be used to identify those features in FIG. 20. As shown in FIG. 20, the instrument 710 includes a hand piece 712 and a blade assembly 714 that extends outwardly from the hand piece 712 to a distal end 718. In the illustrative embodiment, the blade assembly 714 is secured to the hand piece 712 and not configured to be detached. Additionally, the instrument 710 is configured to be disposed after a single use.

The hand piece 712 of the surgical instrument 710 includes an elongated body 722. The body 722 is configured to be grasped by a user during operation of the surgical instrument 710. The elongated body 722 may be formed from a plastic, rigid polymer, or other rigid materials. A cutting slot 716 is positioned at the distal end 718 of the blade assembly 714. This embodiment of the surgical instrument includes a hose 724 that is connected to a vacuum pump (not shown) and a cable 726 that is connected to an electrical source such as, for example, a wall outlet.

Like the instrument 10, the instrument 710 includes an electric motor 728 that is configured to drive the blade assembly 714. In this embodiment, the motor 728 may be activated using a control button 62 positioned on the hand piece 712. A gear assembly (not shown) transmits the output of the motor 728 to the inner blade shaft 100 to cause the inner blade shaft 100 to rotate relative to the outer blade shaft 102 and thereby cut tissue.

It should be appreciated that the size and configuration of each of the instruments and blade assemblies described herein permit the devices to be portable and facilitate the ease of use of the device in surgical procedures.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. For example, it should be understood that the materials used to form the various surgical instruments described herein may be modified or changed to reduce the weight of the instrument and facilitate single-handed use. Similarly, other materials may be selected to reduce friction of the inner passageways and outer surfaces. Still other materials may be selected for their anti-reflective properties. Additionally, as described above, the materials used to form the distal ends of the inner and outer blade shafts are dissimilar metallic materials. It should be appreciated that in other embodiments other dissimilar materials may be used. In still other embodiments, the same materials may be used.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A surgical instrument and cable drive mechanism, comprising:
   a hand piece,
   an outer-most shaft coupled to the hand piece that extends to a distal end, the outer-most shaft having a closed, rounded, convex distal surface and a first plurality of cutting teeth defined at the distal end,
   an inner shaft positioned in the outer-most shaft, the inner shaft having a passageway and a second plurality of cutting teeth, wherein the diameter of the passageway in the distal section is less than the diameter in the proximal section, and wherein the surgical instrument includes a cutting slot that is partially defined by the first plurality of cutting teeth, and the inner shaft is configured to rotate relative to the outer-most shaft such that the first plurality of cutting teeth and the second plurality of cutting teeth cooperate to cut tissue advanced into the passageway through the cutting slot, wherein the instrument is disposable after a single use; and
   a cable drive mechanism coupled to the hand piece and configured to rotate the inner shaft relative to the-most outer shaft.

2. The surgical instrument of claim 1, wherein the outer-most shaft includes a cylindrical outer surface that extends along a longitudinal axis of the outer-most shaft to the rounded, convex distal surface, and the cutting slot is defined in the cylindrical outer surface.

3. The surgical instrument of claim 2, wherein the second plurality of cutting teeth are axially aligned with the cutting slot.

4. The surgical instrument of claim 2, wherein the rounded, convex distal surface extends from a distal apex to a proximal edge, and the proximal edge of the convex distal surface defines a distal end of the cutting slot.

5. The surgical instrument of claim 4, wherein the proximal edge of the rounded, convex distal surface is one of a chamfered edge and a rounded edge.

6. The surgical instrument of claim 4, wherein: the cutting slot extends to a proximal end defined by a distal edge of an outer surface of the outer-most shaft, the proximal edge of the convex distal surface and the distal edge of the outer surface of the outer-most shaft cooperate to define a curved imaginary plane, and the first plurality of cutting teeth are recessed below the curved imaginary plane.

7. The surgical instrument of claim 6, the distal edge of the outer surface is one of a chamfered edge and a rounded edge.

8. The surgical instrument of claim 1, wherein each cutting tooth of the first plurality of cutting teeth includes a planar outer surface.

9. The surgical instrument of claim 1, wherein the hand piece includes a connector configured to be coupled to a negative pressure source to fluidly connect the passageway of the inner shaft to the negative pressure source.

10. The surgical instrument of claim 1, wherein the outer-most shaft and the inner shaft are removably coupled to the hand piece.

11. The surgical instrument of claim 10, further comprising a hub coupled to the outer-most shaft, wherein the hub includes a plurality of splines engaged with the hand piece to secure the outer-most shaft to the hand piece.

12. The surgical instrument of claim 11, further comprising a second hub coupled to the inner shaft, wherein the second hub includes a second plurality of splines engaged with the hand piece to rotatably couple the inner shaft to the hand piece.

13. The surgical cutting tool of claim 1, wherein the cable drive mechanism comprises bi-plex or tri-plex coil drive cables.

14. A surgical instrument and cable drive mechanism, comprising:
   a hand piece,
   an outer-most shaft coupled to the hand piece, the outer-most shaft including (i) a cylindrical outer surface extending along a longitudinal axis of the outer-most shaft, (ii) a closed, rounded, convex distal end, and (iii) a cutting slot defined in the cylindrical outer surface adjacent to the closed distal end, and
   a second shaft positioned in the outer-most shaft, the second shaft having a plurality of cutting teeth axially aligned with the cutting slot, the second shaft having a passageway, wherein the diameter of the passageway in the distal section is less than the diameter in the proximal section, and, wherein the second shaft is configured to rotate relative to the outer-most shaft such that the plurality of teeth cut tissue in the cutting slot, wherein the instrument is disposable after a single use; and a cable drive mechanism coupled to the hand piece and configured to rotate the second shaft relative to the outer-most shaft.

15. The surgical instrument of claim 14, wherein the closed distal end of the outer-most shaft defines a spherical tip.

16. The surgical instrument of claim 15, wherein the second shaft includes a spherical distal tip.

17. The surgical instrument of claim 14, wherein the outer-most shaft is formed from a first material and the second shaft is formed from a second material different from the first material.

18. The surgical instrument of claim 14, wherein a distal section of the outer-most shaft is malleable.

19. The surgical instrument of claim 18, wherein the distal section of the outer-most shaft includes a plurality of slots defined in the first shaft.

20. The surgical instrument of claim 18, wherein a proximal section of the outer-most shaft is substantially rigid.

21. The surgical instrument of claim 14, wherein a distal section of the second shaft is flexible.

22. The surgical instrument of claim 21, wherein a proximal section of the second shaft is substantially rigid.

23. The surgical cutting tool of claim 14, wherein the cable drive mechanism comprises bi-plex or tri-plex coil drive cables.

24. A surgical cutting tool-and cable drive mechanism, comprising:

an outer-most shaft including: (i) a cylindrical outer surface extending along a longitudinal axis of the outer-most shaft to an atraumatic tip, (ii) a first passageway extending along the longitudinal axis from an open proximal end to a closed, rounded, convex distal end, and (iii) a cutting slot extending inward from the cylindrical outer surface to the first passageway, the cutting slot being positioned adjacent to the closed distal end, and a second shaft positioned in the first passageway of the outer-most shaft, the second shaft having a second passageway, wherein the diameter of the second passageway in the distal section is less than the diameter in the proximal section, and a cutting edge that is axially aligned with the cutting slot, wherein the second shaft is configured to rotate relative to the outer-most shaft such that the cutting edge cuts tissue advanced into the second passageway through the cutting slot, wherein the instrument is disposable after a single use; and a cable drive mechanism coupled to the hand piece and configured to rotate the second shaft relative to the outer-most shaft.

25. The surgical cutting tool of claim 24, wherein the cutting slot is partially defined by a plurality of cutting teeth, and the cutting edge and the plurality of cutting teeth cooperate to cut tissue advanced into the second passageway through the cutting slot when the second shaft is rotated.

26. The surgical cutting tool of claim 25, wherein the plurality of cutting teeth are a first plurality of cutting teeth, and the cutting edge includes a second plurality of cutting teeth.

27. The surgical cutting tool of claim 25, wherein the plurality of cutting teeth are recessed from the cylindrical outer surface.

28. The surgical cutting tool of claim 24, wherein the outer-most shaft includes a distal section that defines a first diameter and a proximal section that defines a second diameter greater than the first diameter.

29. The surgical cutting tool of claim 24, wherein the cable drive mechanism comprises bi-plex or tri-plex coil drive cables.

* * * * *